(12) United States Patent  
Koenemann et al.

(10) Patent No.: US 11,987,738 B2  
(45) Date of Patent: May 21, 2024

(54) $C_2$-$C_3$-ALKENYL-SUBSTITUTED RYLENE IMIDE DYES AND CURING PRODUCT OF CURABLE SILICON RESIN COMPOSITION AND $C_2$-$C_3$-ALKENYL-SUBSTITUTED RYLENE IMIDE DYES

(71) Applicants: BASF SE, Ludwigshafen am Rhein (DE); Universitaet des Saarlandes, Saarbrucken (DE)

(72) Inventors: Martin Koenemann, Ludwigshafen (DE); Hannah Stephanie Mangold, Ludwigshafen (DE); Sorin Ivanovici, Ludwigshafen (DE); Nils Steinbrueck, Saarbruecken (DE); Guido Kickelbick, Saarbruecken (DE)

(73) Assignees: BASF SE (DE); UNIVERSITAT DES SAARLANDES (DE)

( * ) Notice: Subject to any disclaimer, the term of this patent is extended or adjusted under 35 U.S.C. 154(b) by 982 days.

(21) Appl. No.: 16/961,118

(22) PCT Filed: Jan. 10, 2019

(86) PCT No.: PCT/EP2019/050492  
§ 371 (c)(1),  
(2) Date: Jul. 9, 2020

(87) PCT Pub. No.: WO2019/137975  
PCT Pub. Date: Jul. 18, 2019

(65) Prior Publication Data  
US 2020/0362235 A1 Nov. 19, 2020

(30) Foreign Application Priority Data  
Jan. 11, 2018 (EP) ..................... 18151250

(51) Int. Cl.  
*C08G 77/442* (2006.01)  
*C07D 471/06* (2006.01)  
(Continued)

(52) U.S. Cl.  
CPC ............ *C09K 11/06* (2013.01); *C07D 471/06* (2013.01); *C08G 77/442* (2013.01); *C09B 69/10* (2013.01);  
(Continued)

(58) Field of Classification Search  
USPC ........................................................ 528/90  
See application file for complete search history.

(56) References Cited

U.S. PATENT DOCUMENTS 9,048,406 B2   6/2015 Yamazaki et al.  
2004/0024151 A1   2/2004 Becker et al.  
(Continued)

FOREIGN PATENT DOCUMENTS

EP         3072887 A1      9/2016  
WO   WO 2012/168395 A1    12/2012  
(Continued)

OTHER PUBLICATIONS

WO-2012168395-A1 Machine Translation (Year: 2012).*  
(Continued)

*Primary Examiner* — Terressa Boykin  
(74) *Attorney, Agent, or Firm* — Faegre Drinker Biddle & Reath LLP

(57) ABSTRACT

The present invention relates to a curable resin composition comprising a curable resin mixture and at least one $C_2$-$C_3$-alkenyl-substituted compound of formula (I) wherein m is 1, 2 or 3; $R^{m1}$, $R^{m2}$, $R^{m3}$ and $R^{m4}$ are hydrogen or $C_6$-$C_{14}$-aryloxy, which is substituted by one or more radicals selected from $C_1$-$C_{24}$-alkyl and $C_6$-$C_{14}$-aryl-$C_1$-$C_{10}$-alkylene; $R^5$, $R^6$, are hydrogen or optionally substituted $C_6$-$C_{14}$-aryl, or $R^5$ and $R^6$ together are a diradical of the formula A; A is a diradical of the formulae A.1 or A.2 wherein $R^7$ is $C_2$-$C_3$-alkenyl; $R^8$, n are as defined in the claims and in the description. The present invention also relates to a polymer comprising in copolymerized form at least one compound of formula (I) and an organopolysiloxane and to novel compounds of formula (I).

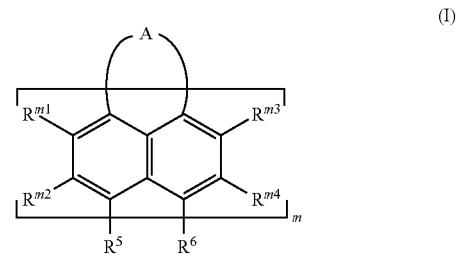

(I)

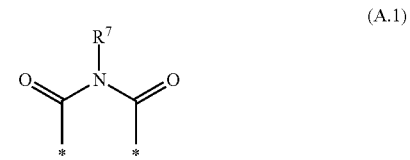

(A.1)

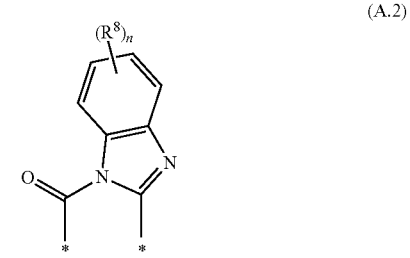

(A.2)

14 Claims, No Drawings

(51) Int. Cl.
*C09B 69/10* (2006.01)
*C09K 11/06* (2006.01)
*H01L 33/50* (2010.01)

(52) U.S. Cl.
CPC .... *H01L 33/502* (2013.01); *C09K 2211/1425* (2013.01); *C09K 2211/1433* (2013.01); *C09K 2211/1466* (2013.01)

(56) References Cited

U.S. PATENT DOCUMENTS

| | | | |
|---|---|---|---|
| 2007/0112147 A1 | 5/2007 | Morita et al. | |
| 2012/0301724 A1* | 11/2012 | Frauenrath | B05D 3/02 427/164 |
| 2014/0021502 A1 | 1/2014 | Shimizu et al. | |
| 2014/0103374 A1 | 4/2014 | Koenemann et al. | |
| 2014/0131740 A1 | 5/2014 | Kang et al. | |
| 2016/0284947 A1 | 9/2016 | Koenemann et al. | |
| 2016/0340510 A1 | 11/2016 | Huang et al. | |

FOREIGN PATENT DOCUMENTS

| | | | |
|---|---|---|---|
| WO | WO-2012168395 A1 * | 12/2012 | ............ C09B 57/06 |
| WO | 2017/121833 A1 | 7/2017 | |

OTHER PUBLICATIONS

International Search Report dated Aug. 2, 2020 in PCT/EP2019/050492, 5 pages.
International Preliminary Report on Patentability and Written Opinion dated Jul. 14, 2020 in PCT/EP2019/050492 (English Translation only), 6 pages.
C. B. Nielsen et al., "Copolymers of Polyethylene and Perylenediimides through Ring-Opening Melathesis Polymerization", Macromolecules, vol. 41, No. 4, XP0555014482008, pp. 1094-1103.
J. Horak et al., "Investigations on the chromatographic behavior of hybrid reversed-phase materials containing electron donor-acceptor systems, II. Contribution of 'IT-'IT aromatic interactions", Journal of Chromato-graphy A, Elsevier: Amsterdam, NL, vol. 1045, No. 1-2, XP004522998, 2004, pp. 43-58.
M. Funahashi et al., "Liquid-crystalline perylene tetracarboxylic bisimide derivatives bearing cyclotetrasiloxane moieties", J. Mat. Chem. C, vol. 1, No. 47, XP055501425, 2013, pp. 7872-7878.
Andreas Decker et al., "Toward Functional Inorganic/Organic Hybrids: Phenoxy-allyl-PTCDI Synthesis, Experimentally and Theoretically Determined Properties of the Isolated Molecule, Layer Characteristics, and the Interface Formation of Phenoxy-allyl-PTCDI on Si(111):H Determined by SXPS and DFT", J. Phys. Chem. C, 2011, 115 (43), pp. 21139-21150.

* cited by examiner

$C_2$-$C_3$-ALKENYL-SUBSTITUTED RYLENE IMIDE DYES AND CURING PRODUCT OF CURABLE SILICON RESIN COMPOSITION AND $C_2$-$C_3$-ALKENYL-SUBSTITUTED RYLENE IMIDE DYES

The present invention relates to $C_2$-$C_3$-alkenyl-substituted rylene imide dyes, to a curable silicone resin composition comprising a curable silicone resin mixture and said $C_2$-$C_3$-alkenyl-substituted rylene imide dye, to a polymer comprising in copolymerized form said rylene imide dye and an organopolysiloxane, to the use of said polymer in the manufacture of an LED device and to a lighting device comprising a blue LED.

BACKGROUND OF THE INVENTION

Nowadays, light emitting diodes (LEDs) are replacing conventional light sources such as incandescent lamps and fluorescent lamps to an ever increasing extent. Lighting devices on the basis of LEDs are used as a source of white light for a wide range of applications, such as for general lighting illumination, architectural, automotive or aviation lighting, as backlight in full-color displays including in flat panel display applications. LED lighting has many advantages, since it has a long lifespan and is very energy efficient.

A widely used technology in producing white light with LEDs is phosphor conversion, where a polymeric material comprising a luminescent material (also referred to as phosphor) is applied directly to the LED light source (blue LED chip, typically emitting at 400 to 480 nm). A configuration in which the phosphor is applied directly and without intervening space to the surface of the LED chip is also referred to as "phosphor on chip" configuration. The phosphor absorbs a proportion of blue light and emit longer-wave light such that the mixing of the blue light transmitted and of the light emitted gives rise to white light. Since these applications require a very high thermal and photochemical stability of the polymeric material and the phosphors, the phosphors most commonly used are inorganic oxides doped with rare earth ions. The most widely used and commerically available white LED is based on the emission of blue light from an InGaN chip coated with cerium-doped yttrium aluminium garnet (Ce:YAG) phosphor (emission in the yellow spectral range (around 560 nm)). This design is especially suitable for high-power and high stability applications. These LEDs, however, suffer from a lack of red emission, high correlated color temperature and low color rendering index. To overcome this disadvantage, a blend of yellow phosphor and red phosphor (wavelength longer than 600 nm) may be used. Known red phosphors such as nitride phosphors, however, suffer from insufficient stability. An LED device is usually composed of the LED chip fabricated onto a substrate and then encapsulated by a material acting as a lens. The material to be suitable as an encapsulant of LEDs must have high temperature resistance, and optical clarity. Typically, the blue LED chip is encapsulated with a polymeric resin comprising the phosphor(s). Initially, epoxy resin was used as encapsulation material. The major disadvantages of epoxy resin as encapsulation material are its degradation under exposure to radiation and high temperatures which results in yellowing in time. Nowadays, addition-curable silicone resins (organopolysiloxane resins) are widely used as transparent resins. Addition-curable silicone resins do not generate any by-products in hydrosilylation reactions of alkenylsilyl groups with hydrosilyl groups and provide cured products with good thermal stability, chemical inertness, moisture resistance, oxidation resistance, good adhesion to surfaces and tunable refractive indices by appropriate side group substitution. Therefore, curable silicone resins are used for LED encapsulation. In the LED industry, two general types are used, one is based on low refractive index poly(dimethyl siloxane), namely LRI silicone also known as methyl silicone. The other is high refractive index polymethylphenylsiloxane, namely HRI silicone also known as phenyl silicone.

In order to circumvent the above-mentioned lighting quality and color rendering issues, organic phosphors can be used in producing white light with LEDs by phosphor conversion. Since organic phosphors are sensitive to the heat generated during electroluminescence activity of the LED, they are mainly used in remote phosphor configuration, i.e. a color converter (also referred to simply as "converter"), which generally comprises the organic phosphor, a polymer matrix and optionally a carrier, is at a certain distance from the LED chip.

The use of organic phosphors (also referred to as organic fluorescent dyes) offers various advantages. Organic fluorescent dyes are much higher-yielding due to their significantly higher mass-specific absorption, which means that considerably less material is required for efficient radiation conversion than in the case of inorganic phosphors. They also have a high efficiency. In addition, they allow to tailor the hue of the light, since their emission spectrum often is tunable. Furthermore, they do not require any materials comprising rare earths, which have to be mined and provided in a costly and inconvenient manner and are available only to a limited degree.

The compound N,N'-diallyl-1,6,7,12-tetraphenoxyperylene-3,4:9,10-tetracarboxylic acid diimide is known from J. Phys. Chem C, 2011, 115 (43), pp 21139-21150. The compound can be used as a sensitizer in thin film silicon solar cells.

N,N'-Diallylperylene-3,4,9,10-tetracarboxylic bisimide is described in J. Mater. Chem. C, 2013, 1, 7872-7878 as intermediate compound in the preparation of liquid-crystalline (LC) perylene tetracarboxylic bisimide derivatives bearing cyclotetrasiloxane moieties which exhibit high electron mobility. An incorporation of perylenetetracarboxylic bisimide compounds bearing alkenyl chains in a curable polysiloxane matrix is not described.

N,N'-Diallyl-1,7-bis(4-tert-butylphenoxy)perylene-3,4,9,10-tetracarboxdiimide is described in Macromolecules 2008, 41, 1094-1103. Metathesis polymerization of cis-cyclooctene with said compound enables incorporation of the perylenediimide dye molecule into an unsaturated polycyclooctene chain. Subsequent hydrogenation of the copolymer affords a high molecular polyethylene-perylenediimide copolymer.

Jeannie Horak, Norbert M. Maier and Wolfgang Lindner describe in Journal of Chromatography A, 2004, vol. 1045, pages 43-58, mono-alkenyl naphthalene imides and dialkenyl naphthalene bisimides immobilized onto 3-propylthiol silica gel support.

US 2004/0024151 describes functionalized perylene tetracarboxylic acid diimides as initiator for various polymerization reactions or as co-reactants in polymer-analogous reactions. The perylene-3,4,9,10-tetracarboxylic acid diimide compounds have at least one radical containing a functional group in positions 1, 6, 7 and/or 12, with the functional group forming a covalent bond in a polymerization reaction. It is said that the perylene compounds are covalently bonded into the polymer formed. The perylene tetracarboxylic acid diimides covalently bonded into the polymer may be used in fluorescent solar collectors, as laser dye, in greenhouse sheeting, for optical and/or opto-electronic applications, as fluorescent label or fluorescent probe.

US 2012/0301724 describes polymer-substituted organic fluorescent dyes, containing a fluorescent core, wherein the dye is substituted with at least one polymer segment P. The fluorescent core is selected from naphthalenes, perylenes, terrrylenes, quaterrylenes which is optionally substituted and the polymer segment is selected from poly(styrene), poly(methyl methacrylate), poly(butyl methacrylate), poly(butyl acrylate), poly(isoprene), poly(butadiene), hydrogenated poly(isoprene), poly(cyclooctene), poly(tetrafluoroethylene) and its copolymers, or poly(isobutylene). The organic fluorescent may furthermore comprise a linking group between the fluorescent core and the polymer, said linking group being an imide, amide, ester, amine or an heteroatom O. A spacer group may also be present between the polymer and the linking group and/or between the fluorescent core and the linking group. Preferred are poly(isobutylene)-substituted fluorescent dyes. All exemplified polymer-substituted naphthalene and rylene dyes are unsubstituted on the fluorescent core. This document also describes color conversion films comprising said polymer-substituted organic fluorescent dyes and a matrix polymer such as a hydrophobic polymer.

WO 2012/168395 describes organic fluorescent dyes comprising at least one structural unit of the formula A

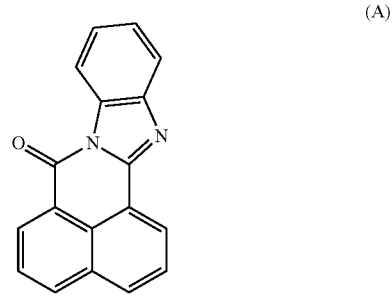

(A)

where the structural unit may be mono- or polysubstituted by identical or different substituents, which may be chemically bounded to a polymer P such as polyetherols, polyesterols or polycarbonates.

However, organic fluorescent dyes of prior art often suffer from a lack of the required long-term thermal and chemical stability when submitted to the harsh conditions encountered in blue LED based lighting devices. Further drawbacks are, for example, irreversible leaching or bleeding out of the organic fluorescent dyes from the polymer matrix, and aggregation of the organic fluorescent dye during operation of LEDs leading to inhomogeneous distribution of the organic fluorescent dye(s) within the polymer matrix. The aggregation of the organic fluorescent dye reduces absorption and fluorescence quantum yield which in turn causes undesired color point shift.

There is a need to replace inorganic fluorescent colorants against organic counterparts for the reduction of rare earth elements in LED-based lighting applications. There is especially a need for a castable curable silicone resin including the organic fluorescent dye for use with LED devices. There is also a need to provide lighting devices with improved durability which can be easily manufactured.

Accordingly, it is an object of the present invention to provide fluorescent silicone resins for use in LED applications.

Alternatively or additionally, it is an object of the present invention to provide organic fluorescent dyes which can be covalently incorporated into a silicone resin.

Alternatively or additionally, it is an object to provide a lighting device, wherein a fluorescent material is disposed in front of the blue LED in its emission direction and where the fluorescent material is not spaced from the LED.

Preferably, the fluorescent material should also feature one or more of the following characteristics:

high fluorescence quantum yield (QY) of at least 80%;

long-term photostability under blue light irradiation conditions;

long-term stability towards heat, oxygen and moisture under blue light irradiation conditions; and easy preparation.

These and further objectives are achieved by the compounds of formula (I) as defined herein below. The present inventors also found that a colored silicone resin composition with excellent dye stability can be obtained by mixing a curable silicone resin composition with a compound of formula (I) as fluorescent dye.

SUMMARY OF THE INVENTION

Therefore, in a first aspect the present invention relates to a curable silicone resin composition comprising a curable silicone resin mixture and at least one $C_2$-$C_3$-alkenyl-substituted compound of formula (I)

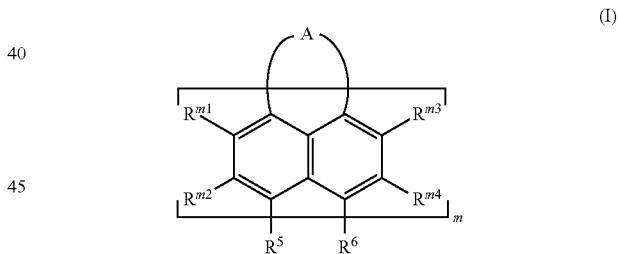

(I)

wherein m is 1, 2 or 3;

each $R^{m1}$, $R^{m2}$, $R^{m3}$ and $R^{m4}$, independently of one another, are hydrogen or $C_6$-$C_{14}$-aryloxy, which is substituted by one or more radicals selected from $C_1$-$C_{24}$-alkyl and $C_6$-$C_{14}$-aryl-$C_1$-$C_{10}$-alkylene, where the aryl moiety of $C_6$-$C_{14}$-aryl-$C_1$-$C_{10}$-alkylene is unsubstituted or substituted by one or more $C_1$-$C_{10}$-alkyl and the alkylene moiety of $C_6$-$C_{14}$-aryl-$C_1$-$C_{10}$-alkylene may be interrupted by one or more groups selected from O, S and $NR^a$;

$R^5$, $R^6$, independently of each other, are hydrogen or $C_6$-$C_{14}$-aryl, wherein aryl is unsubstituted or substituted with one or two $C_2$-$C_3$-alkenyl groups and 0, 1, 2, 3, 4 or 5 identical or different radicals $R^{5a}$ or $R^5$ and $R^6$ together are a diradical of the formula A;

A is a diradical of the formulae (A.1) or (A.2),

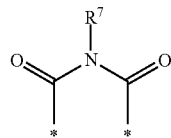

(A.1)

(A.2)

wherein
* in each case denotes the point of attachments to the naphthalene skeleton;
n is 0, 1, 2, 3 or 4;
$R^7$ is $C_2$-$C_3$-alkenyl;
each $R^8$ is $C_1$-$C_{24}$-alkyl, $C_2$-$C_3$-alkenyl, $C_3$-$C_{14}$-cycloalkyl, $C_6$-$C_{14}$-aryl, $C_6$-$C_{14}$-aryl-$C_1$-$C_{10}$-alkylene where the rings of cycloalkyl, aryl, and aryl-alkylene in the three last-mentioned radicals are unsubstituted or substituted with one or two $C_2$-$C_3$-alkenyl groups and 0, 1, 2, 3, 4 or 5 identical or different radicals $R^{8a}$ and where $C_1$-$C_{24}$-alkyl and the alkylene moiety of $C_6$-$C_{14}$-aryl-$C_1$-$C_{10}$-alkylene may be interrupted by one or more groups selected from O, S and $NR^a$;
$R^{5a}$, is $C_1$-$C_{24}$-alkyl, $C_6$-$C_{14}$-aryl or $C_6$-$C_{14}$-aryl which is substituted with $C_2$-$C_3$-alkenyl;
$R^{8a}$, is independently of one another, are $C_1$-$C_{24}$-alkyl, $C_2$-$C_3$-alkenyl, $C_6$-$C_{14}$-aryl or $C_6$-$C_{14}$-aryl which is substituted with $C_2$-$C_3$-alkenyl;
$R^a$ is hydrogen, $C_1$-$C_{20}$-alkyl, $C_3$-$C_{24}$-cycloalkyl or and $C_6$-$C_{14}$-aryl;
with the proviso that the compound of formula (I) comprises 1, 2, 3 or 4 $C_2$-$C_3$-alkenyl groups.

In a further aspect of the present invention, provided herein are novel compounds of formulae (I-A.1) and (I-A.2),

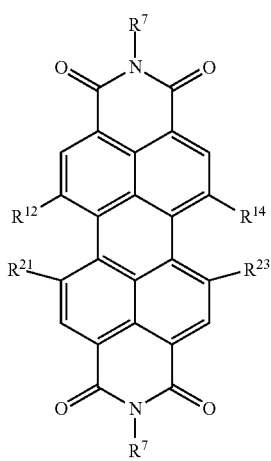

(I-A.1)

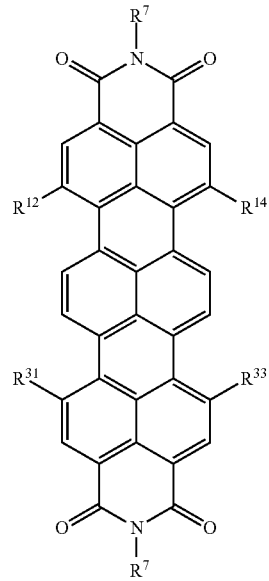

(I-A.2)

wherein
each $R^7$ is, independently of each other, selected from vinyl or 2-propenyl;
at least one of $R^{12}$, $R^{14}$, $R^{21}$, $R^{23}$, $R^{31}$, $R^{33}$ is phenoxy, which is substituted by one, two or three radicals selected from branched $C_3$-$C_{24}$-alkyl, linear $C_6$-$C_{24}$-alkyl and phenyl-$C_1$-$C_{10}$-alkylene, where the phenyl moiety of phenyl-$C_1$-$C_{10}$-alkylene is unsubstituted or substituted by one, two or three $C_1$-$C_{10}$-alkyl; and
the remaining radicals $R^{12}$, $R^{14}$, $R^{21}$, $R^{23}$, $R^{31}$, $R^{33}$, independently of each are hydrogen or phenoxy, which is substituted by one, two or three radicals selected from branched $C_3$-$C_{24}$-alkyl, linear $C_6$-$C_{24}$-alkyl and phenyl-$C_1$-$C_{10}$-alkylene, where the phenyl moiety of phenyl-$C_1$-$C_{10}$-alkylene is unsubstituted or substituted by one, two or three $C_1$-$C_{10}$-alkyl;
except for the compound N,N'-diallyl-1,7-bis(4-tert-butylphenoxy)perylene-3,4:9,10-tetracarboxydiimide.

In a further aspect of the present invention, provided herein are novel compounds of formula (I-B)

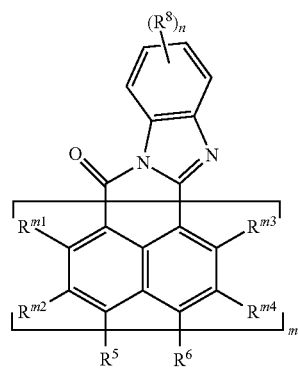

(I-B)

wherein
m is 1 or 2;
n is 1, 2 or 3;
each $R^8$ is $C_1$-$C_{24}$-alkyl, $C_2$-$C_3$-alkenyl, $C_3$-$C_{14}$-cycloalkyl, $C_6$-$C_{14}$-aryl, $C_6$-$C_{14}$-aryl-$C_1$-$C_{10}$-alkylene where the rings of cycloalkyl, aryl, and aryl-alkylene in the three last-mentioned radicals are unsubstituted or substituted with one or two $C_2$-$C_3$-alkenyl groups and 0, 1, 2, 3, 4 or 5 identical or different radicals $R^{8a}$ and where $C_1$-$C_{24}$-alkyl and the alkylene moiety of $C_6$-$C_{14}$-aryl-$C_1$-$C_{10}$-alkylene may be interrupted by one or more groups selected from O, S and $NR^a$;

each $R^{m1}$, $R^{m2}$, $R^{m3}$ and $R^{m4}$, independently of one another, are hydrogen or $C_6$-$C_{14}$-aryloxy, which is substituted by one or more radicals selected from $C_1$-$C_{24}$-alkyl and $C_6$-$C_{14}$-aryl-$C_1$-$C_{10}$-alkylene, where the aryl moiety of $C_6$-$C_{14}$-aryl-$C_1$-$C_{10}$-alkylene is unsubstituted or substituted by one or more $C_1$-$C_{10}$-alkyl and the alkylene moiety of $C_6$-$C_{14}$-aryl-$C_1$-$C_{10}$-alkylene may be interrupted by one or more groups selected from O, S and $NR^a$;

$R^5$, $R^6$, independently of each other, are hydrogen or $C_6$-$C_{14}$-aryl, wherein aryl is unsubstituted or substituted with one or two $C_2$-$C_3$-alkenyl groups and 0, 1, 2, 3, 4 or 5 identical or different radicals $R^{5a}$, or $R^5$ and $R^6$ together are a diradical of the formula A.2

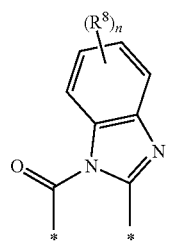

(A.2)

wherein each $R^8$ is $C_1$-$C_{24}$-alkyl, $C_2$-$C_3$-alkenyl, $C_3$-$C_{14}$-cycloalkyl, $C_6$-$C_{14}$-aryl, $C_6$-$C_{14}$-aryl-$C_1$-$C_{10}$-alkylene where the rings of cycloalkyl, aryl, and aryl-alkylene in the three last-mentioned radicals are unsubstituted or substituted with one or two $C_2$-$C_3$-alkenyl groups and 0, 1, 2, 3, 4 or 5 identical or different radicals $R^{8a}$ and where $C_1$-$C_{24}$-alkyl and the alkylene moiety of $C_6$-$C_{14}$-aryl-$C_1$-$C_{10}$-alkylene may be interrupted by one or more groups selected from O, S and $NR^a$;

$R^{5a}$, is $C_1$-$C_{24}$-alkyl, $C_6$-$C_{14}$-aryl or $C_6$-$C_{14}$-aryl which is substituted with $C_2$-$C_3$-alkenyl;

$R^{8a}$, is $C_1$-$C_{24}$-alkyl, $C_2$-$C_3$-alkenyl, $C_6$-$C_{14}$-aryl or $C_6$-$C_{14}$-aryl which is substituted with $C_2$-$C_3$-alkenyl;

$R^a$ is hydrogen, $C_1$-$C_{20}$-alkyl, $C_3$-$C_{24}$-cycloalkyl or and $C_6$-$C_{14}$-aryl;

with the proviso that the compound of formula (I-B) comprises 1, 2, 3 or 4 $C_2$-$C_3$-alkenyl groups.

In a further aspect of the present invention, provided herein is a polymer comprising in copolymerized form (a) at least one compound of formula (I) as defined above and (b) an organopolysiloxane C.

In a further aspect of the present invention, provided herein is the use of a polymer as defined above in the manufacture of an LED device.

In a further aspect of the present invention, provided herein is a lighting device, comprising a blue LED with a center wavelength of emission between 400 nm and 480 nm and a polymer as defined above, wherein the polymer is disposed in front of the LED in its emission direction and where the polymer is not spaced from the LED.

DESCRIPTION OF THE INVENTION

The compounds of formula (I) are characterized by an aromatic core formed by a rylene system, i.e. a naphthalene system for m=1; a perylene system for m=2, and a terrylene system for m=3. In the compounds of formula (I), m is the number of naphthalene units. In the individual variables $R^{m1}$ to $R^{m4}$, m is the particular naphthalene group of the rylene skeleton to which the variables are bonded. Variables $R^{m1}$ to $R^{m4}$ which are bonded to different naphthalene groups may each have the same or different meanings.

Accordingly, the compounds of formula (I) may be represented by the following formulae:

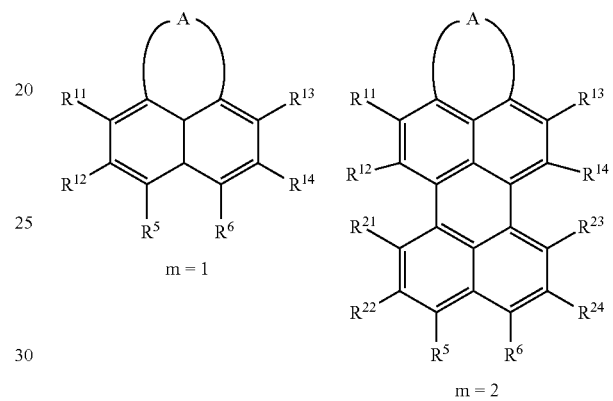

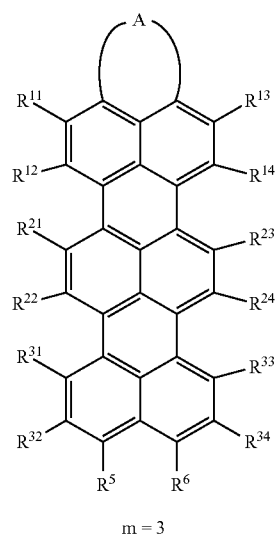

In the compounds of formula (I), wherein A is a group of the formula (A.2), and $R^5$ and $R^6$ together are a diradical (A.2), the two groups (A.2) can be bound either syn or anti with regard to the rylene system. Accordingly, the compounds of the formula I, where m=1, 2 or 3 may have the following formulae:

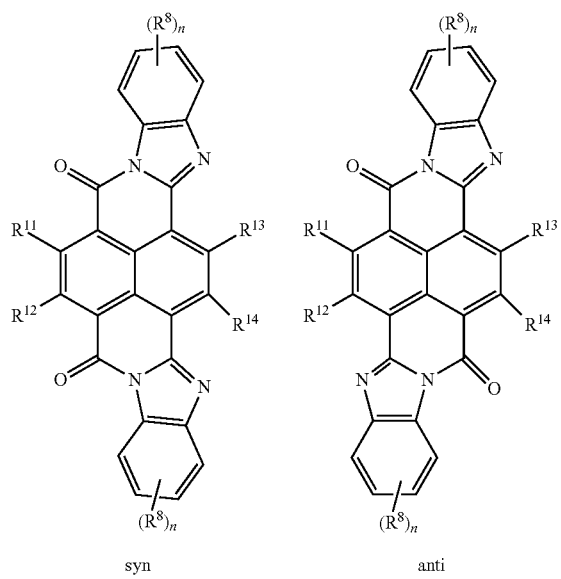

syn  anti m = 1

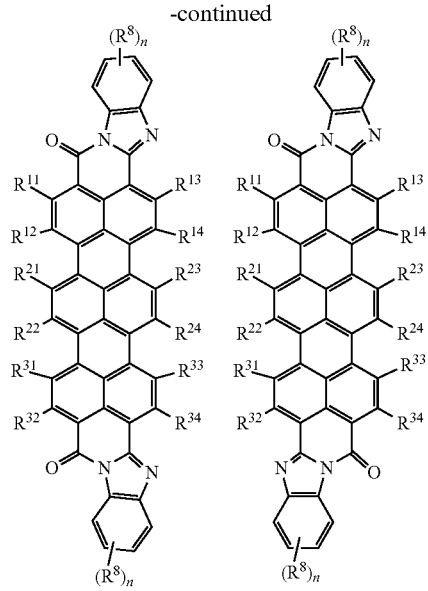

syn  anti m = 3

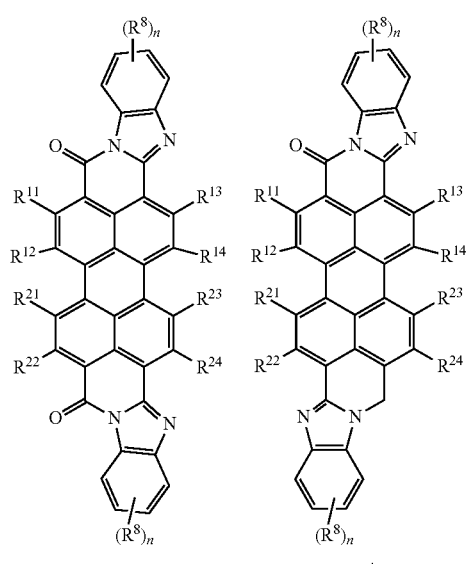

syn  anti m = 2

Fluorescent colorants include all materials which are capable of absorbing light of a particular wavelength and converting it to light of another longer wavelength.

In the context of the present invention, the term "phosphor" (also referred to as "fluorescent colorant" or simply "colorant") refers to a solid material which converts light of a first wavelength to light of a second different wavelength. The phosphor may be inorganic or organic. According to the color of light (wavelength of light), the phosphor may be classified as green, yellow, orange, red one, etc. The term "phosphor" is to be understood as including a single phosphor compound or a phosphor blend or composition of two or more phosphor compounds chosen to produce a selected wavelength conversion.

In the context of the present invention, the terms "organic phosphor", "organic fluorescent colorant" and "organic colorant", are used interchangeably. Organic fluorescent colorants may be organic fluorescent pigments or organic fluorescent dyes. In particular, they are organic fluorescent dyes.

The term "conversion material" refers to a material that is excited by a photon of a first wavelength and emits photons of a second (longer), different wavelength.

A quantum dot is a nanocrystal made of semiconductor materials that is small enough to exhibit quantum mechanical properties. Quantum dots are showing remarkably narrow emission spectra, i.e. with extraordinary small FWHM (full width of half maximum). The color output of the dots can be tuned by controlling the size of the crystals. With a smaller size in quantum dots, the quantum dots emit light of a shorter wavelength.

In the context of the present invention, the term "polymer matrix" refers to a polymer in which the phosphor material is dispersed or molecularly dissolved.

In the context of the present invention, the term "color converter" which is also referred to simply as "converter", is understood to mean all physical devices capable of absorbing light of particular wavelengths and converting it to light of a second wavelength. Color converters are, for example, part of lighting devices, especially those lighting devices which utilize blue LEDs as light source.

In the context of the present invention, the term "center wavelength" of a given spectral distribution $F(\lambda)$ is defined as the following average: $\lambda_c = \int \lambda \cdot F(\lambda) \, d\lambda / \int F(\lambda) \, d\lambda$.

In the context of the present invention, the term "fluorescence quantum yield (QY)" is defined as ratio of the number of photons emitted to the number of photons absorbed.

In the context of the present invention, a "blue LED" is understood to mean an LED which emits light in the blue range of the electromagnetic spectrum with a center wavelength of emission in the range of 400 to 480 nm, preferably 420 to 480, more preferably 440 to 475 nm, most preferably at 440 to 460 nm. Suitable semiconductor materials are silicon carbide, zinc selenide and nitrides such as aluminum nitride (AlN), gallium nitride (GaN), indium nitride (InN) and indium gallium nitride (InGaN). LEDs typically have a narrow wavelength distribution that is tightly centered about their peak wavelength. Standard InGaN-based blue LEDs are fabricated on a sapphire substrate and peak emission wavelength is usually centered at 445 to 455 nm.

In the context of the present invention, the term "white light" relates to light having a correlated color temperature (CCT) between 2 000 to 20 000 K, especially 2 500 to 20 000 K. A commercially available white LED often has a correlated color temperature of 3 000 K or above, for example in the range of 3 000 to 20 000 K or 4° 000 to 20° 000 K.

In the context of the present invention, an electromagnetic radiation comprising the visible spectral range is also designated as light.

As used in this specification and the claims, the singular form "a", "an" and "the" includes plural references unless the content clearly dictates otherwise.

The definitions of the variables specified in the above formula use collective terms which are generally representative of the respective substituents. The definition $C_n$-$C_m$ gives the number of carbon atoms possible in each case in the respective substituent or substituent moiety.

The expression "halogen" denotes in each case fluorine, bromine, chlorine or iodine, particularly chlorine, bromide or iodine.

The term "alkyl" as used herein refers to saturated straight-chain or branched hydrocarbon radicals having usually 1 to 24 ("$C_1$-$C_{24}$-alkyl"), 1 to 18 ("$C_1$-$C_{18}$-alkyl"), 1 to 12 ("$C_1$-$C_{12}$-alkyl"), 1 to 8 ("$C_1$-$C_8$-alkyl") or 6 to 24 ("$C_6$-$C_{24}$-alkyl") carbon atoms.

Examples of alkyl groups are especially methyl, ethyl, n-propyl, isopropyl, n-butyl, isobutyl, sec-butyl, tert-butyl, n-pentyl, 1-methylbutyl, 1-ethylpropyl, neo-pentyl, n-hexyl, 1-methylpentyl, 2-methylpentyl, 1-ethylbutyl, 2-ethylbutyl, n-heptyl, 1-methylhexyl, 2-methylhexyl, 1-ethylpentyl, 1-propylbutyl, 2-ethylpentyl, n-octyl, 1-methylheptyl, 2-methylheptyl, 1-ethylhexyl, 2-ethylhexyl, 1-propylpentyl, 2-propylpentyl, n-nonyl, n-decyl, etc.

The term "alkylene" (or alkanediyl) as used herein in each case denotes an alkyl radical as defined above, wherein one hydrogen atom at any position of the carbon backbone is replaced by one further binding site, thus forming a bivalent moiety.

The term "$C_6$-$C_{14}$-aryl-$C_1$-$C_{10}$-alkylene" (which may also be referred to as aralkyl) as used herein refers to $C_6$-$C_{14}$-aryl-substituted alkyl radicals having at least one unsubstituted or substituted aryl group, as defined herein. The alkyl group of the aralkyl radical may be interrupted by one or more nonadjacent groups selected from O, S and $NR^a$, wherein $R^a$ is as defined above. $C_6$-$C_{14}$-aryl-$C_1$-$C_{10}$-alkylene is preferably phenyl-$C_1$-$C_{10}$-alkylene, more preferably phenyl-$C_1$-$C_4$-alkylene, for example benzyl, 1-phenethyl, 2-phenethyl, 1-phenprop-1-yl, 2-phenprop-1-yl, 3-phenprop-1-yl, 1-phenbut-1-yl, 2-phenbut-1-yl, 3-phenbut-1-yl, 4-phenbut-1-yl, 1-phenbut-2-yl, 2-phenbut-2-yl, 3-phenbut-2-yl or 4-phenbut-2-yl; preferably benzyl and 2-phenethyl.

The term "cycloalkyl" as used herein denotes in each case a mono-, bi- or tricyclic cycloaliphatic radical having usually from 3 to 14 carbon atoms ("$C_3$-$C_{14}$-cycloalkyl"), preferably 3 to 10 carbon atoms ("$C_3$-$C_{10}$-cycloalkyl") or in particular 3 to 6 carbon atoms ("$C_3$-$C_6$-cycloalkyl"). Examples of monocyclic radicals having 3 to 6 carbon atoms comprise cyclopropyl, cyclobutyl, cyclopentyl and cyclohexyl. Examples of monocyclic radicals having 3 to 7 carbon atoms comprise cyclopropyl, cyclobutyl, cyclopentyl, cyclohexyl and cycloheptyl. Examples of bicyclic radicals having 7 or 8 carbon atoms comprise bicyclo[2.1.1]hexyl, bicyclo[2.2.1]heptyl, bicyclo[3.1.1]heptyl, bicyclo[2.2.1]heptyl, bicyclo[2.2.2]octyl and bicyclo[3.2.1]octyl. An example of a tricyclic radical is adamantyl.

The term "$C_2$-$C_3$-alkenyl" as used herein refers to ethenyl (vinyl), 1-propenyl and 2-propenyl (allyl).

For the purpose of the present invention, the term "aryl" refers to a monocyclic aromatic hydrocarbon radical (i.e. phenyl) or fused bi-, tri- or polycyclic aromatic hydrocarbon radical having at least one fused phenyl ring. The number of carbon ring atoms in an aryl group can vary and is ordinarily 6 to 14. If aryl is not a monocyclic aromatic hydrocarbon radical, i.e. phenyl, the term includes for the fused ring(s) the saturated form (perhydro form), the partly unsaturated form (for example the dihydro form or tetrahydro form) or the aromatic form. The term "aryl" includes, for example bicyclic aromatic radicals in which both rings are aromatic and bicyclic aromatic radicals in which only one ring is aromatic. Examples of bi- or tricyclic aromatic carbocycles include naphthyl, 1,2-dihydronaphthyl, 1,4-dihydronaphthyl, 1,2,3,4-tetrahydronaphthyl, indanyl, indenyl, anthracenyl, fluorenyl etc. Preferably, the term "aryl" denotes phenyl and naphthyl.

In the context of the present invention, the terms "radical" and "variable" are used interchangeable.

When # or * appear in a formula showing a substructure of a compound of the present invention, it denotes the attachment bond to the remaining part of the compound.

The remarks made below as to preferred embodiments of the variables (substituents) of the compounds of formula (I) are valid on their own as well as preferably in combination with each other.

The remarks made below concerning preferred embodiments of the variables further are valid on their own as well as preferably in combination with each other concerning the compounds of formula (I), where applicable, as well as concerning the uses according to the invention.

The curable silicone resin composition according to the present invention includes as essential component at least one compound of formula (I).

Preferred are compounds of formula (I) comprising 1, 2 or 3 $C_2$-$C_3$-alkenyl groups.

Preferred are compounds of formula (I), wherein A is a diradical of formula (A.1). In the context of the diradical (A.1), $R^7$ is preferably vinyl or 2-propenyl. More preferably, $R^7$ is 2-propenyl (allyl).

Likewise preferred are compounds of formula (I), wherein A is a diradical of formula (A.2). In the context of the diradical (A.2), n is preferably 1, 2 or 3. In the context of the diradical (A.2), each $R^8$ is preferably selected from $C_1$-$C_{24}$-alkyl, $C_2$-$C_3$-alkenyl, $C_6$-$C_{10}$-aryl and $C_6$-$C_{10}$-aryl-$C_1$-$C_{10}$-alkylene, where the rings of aryl and aryl-alkylene in the two last-mentioned radicals are unsubstituted or substituted with one or two $C_2$-$C_3$-alkenyl groups and 0, 1, 2 or 3 identical or different radicals $R^{8a}$ and where $C_1$-$C_{24}$-alkyl and the alkylene moiety of $C_6$-$C_{10}$-aryl-$C_1$-$C_{10}$-alkylene may be interrupted by one or more, e.g. 1, 2, 3, 4 or more than 4, groups selected from O, S and $NR^a$. The variable $R^{8a}$ has one of the meanings mentioned herein. In particular, $R^8$ is independently selected from $C_6$-$C_{10}$-aryl and $C_6$-$C_{10}$-aryl which is substituted with one or two $C_2$-$C_3$-alkenyl groups selected from vinyl and 2-propenyl.

Preferred are compounds of formula (I), wherein $R^{m1}$, $R^{m2}$, $R^{m3}$ and $R^{m4}$ are selected from hydrogen and $C_6$-$C_{10}$-aryloxy, which is substituted by one or more radicals selected from $C_1$-$C_{24}$-alkyl and $C_6$-$C_{10}$-aryl-$C_1$-$C_{10}$-alkylene, where the aryl moiety of $C_6$-$C_{10}$-aryl-$C_1$-$C_{10}$-alkylene is unsubstituted or substituted by one or more $C_1$-$C_{10}$-alkyl and the alkylene moiety of $C_6$-$C_{10}$-aryl-$C_1$-$C_{10}$-alkylene may be interrupted by one or more, e.g. 1, 2 or 3, groups selected from O, S and $NR^a$. Preferably, at least one of the variables $R^{m1}$, $R^{m2}$, $R^{m3}$ and $R^{m4}$ is hydrogen.

Preferred are compounds of formula (I), wherein $R^5$ and $R^6$, independently of each other, are selected from hydrogen and $C_6$-$C_{10}$-aryl, wherein aryl is unsubstituted or substituted with one or two $C_2$-$C_3$-alkenyl groups and 0, 1, 2, 3, 4 or 5 identical or different radicals $R^{5a}$, wherein $R^{5a}$ has one of the meanings mentioned herein. Likewise preferred are compounds of formula (I), wherein $R^5$ and $R^6$ together are a diradical of the formula A, wherein A has one of the herein defined meanings.

$R^a$, if present, is preferably hydrogen or $C_1$-$C_{10}$-alkyl.

$R^{5a}$, if present, is preferably $C_1$-$C_{24}$-alkyl, $C_6$-$C_{10}$-aryl or $C_6$-$C_{10}$-aryl which is substituted with $C_2$-$C_3$-alkenyl.

$R^{8a}$, if present, is preferably $C_1$-$C_{10}$-alkyl, $C_2$-$C_3$-alkenyl, $C_6$-$C_{10}$-aryl or $C_6$-$C_{10}$-aryl substituted with $C_2$-$C_3$-alkenyl. More preferably, $R^{8a}$, if present, is $C_1$-$C_{10}$-alkyl, vinyl, 2-propenyl, phenyl, phenyl substituted with vinyl or phenyl substituted with 2-propenyl.

Compounds of formula (I), wherein the variable A is a diradical of formula (A.1), have the following formula (I.a), where the index m and the variables $R^5$, $R^6$, $R^7$, $R^{m1}$, $R^{m2}$, $R^{m3}$ and $R^{m4}$ have one of the herein defined meanings.

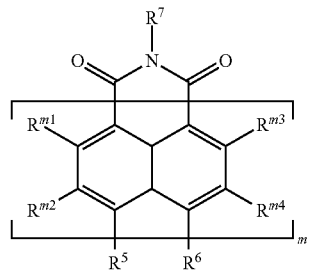

(I.a)

Preferred are compounds of formula (I.a), wherein the variables $R^{m1}$, $R^{m2}$, $R^{m3}$, $R^{m4}$, $R^5$, $R^6$, $R^7$ and the index m independently of one another and preferably in combination preferably have the meanings given below:
$R^7$ is $C_2$-$C_3$-alkenyl; in particular vinyl or 2-propenyl;
$R^5$ and $R^6$ together are a diradical of formula (A.1);
m is 1, 2 or 3; and
at least one of the variables $R^{m1}$, $R^{m2}$, $R^{m3}$ and $R^{m4}$ is hydrogen and at least one of the remaining variables $R^{m1}$, $R^{m2}$, $R^{m3}$ and $R^{m4}$ is $C_6$-$C_{10}$-aryloxy, which is substituted by one or more, e.g. 1, 2 or 3, radicals selected from $C_1$-$C_{24}$-alkyl and $C_6$-$C_{10}$-aryl-$C_1$-$C_{10}$-alkylene, where the aryl moiety of $C_6$-$C_{10}$-aryl-$C_1$-$C_{10}$-alkylene is unsubstituted or substituted by one or more $C_1$-$C_{10}$-alkyl and the alkylene moiety of $C_6$-$C_{10}$-aryl-$C_1$-$C_{10}$-alkylene may be interrupted by one or more, e. g. 1, 2, 3, 4 or more than 4, groups selected from O, S and $NR^a$. In particular, at least one of the variables $R^{m1}$, $R^{m2}$, $R^{m3}$ and $R^{m4}$ is phenyloxy, which is substituted by one or more, e.g. 1, 2 or 3, radicals selected from linear $C_1$-$C_{24}$-alkyl, branched $C_3$-$C_{24}$-alkyl and phenyl-$C_1$-$C_{10}$-alkylene, where the phenyl moiety of phenyl-$C_1$-$C_{10}$-alkylene is unsubstituted or substituted by one or more, e.g. 1, 2, or 3, $C_1$-$C_{10}$-alkyl and the alkylene moiety of phenyl-$C_1$-$C_{10}$-alkylene may be interrupted by one or more groups selected from O, S and $NR^a$. Even more in particular, at least two of the variables $R^{m1}$, $R^{m2}$, $R^{m3}$ and $R^{m4}$ are hydrogen and the remaining variables $R^{m1}$, $R^{m2}$, $R^{m3}$ and $R^{m4}$ have the same meaning and are especially phenyloxy, which is substituted by one, two or three linear $C_6$-$C_{24}$-alkyl, branched $C_3$-$C_{24}$-alkyl and phenyl-$C_1$-$C_{10}$-alkylene, where the phenyl moiety of phenyl-$C_1$-$C_{10}$-alkylene is unsubstituted or substituted by one or more, e.g. 1, 2 or 3, $C_1$-$C_{10}$-alkyl.

Examples for linear $C_6$-$C_{24}$-alkyl are n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, etc.

Examples for phenyl-$C_1$-$C_{10}$-alkylene are benzyl, phenethyl, 3-phenylpropyl, etc.

Examples for branched $C_3$-$C_{24}$-alkyl are a radical of formula (C.1), a radical of formula (C.2), a radical of formula (C.3) and a radical of formula (C.4)

(C.1)

(C.2)

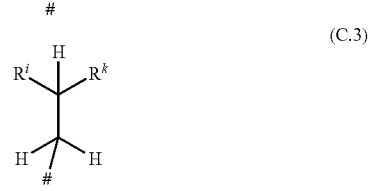

(C.3)

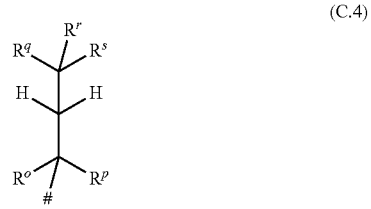

(C.4)

in which # represents the bonding site to the nitrogen atom;

$R^d$ and $R^e$, in the formula (C.1), independently from each other are selected from the group consisting of $C_1$-$C_{22}$- alkyl, where the sum of the carbon atoms of the $R^d$ and $R^e$ radicals is an integer from 2 to 23;

$R^f$, $R^g$ and $R^h$, in the formula (C.2) are independently selected from the group consisting of $C_1$- to $C_{21}$-alkyl, where the sum of the carbon atoms of the $R^f$, $R^g$ and $R^h$ radicals is an integer from 3 to 23;

$R^i$ and $R^k$, in the formula (C.3) are independently selected from the group consisting of $C_1$- to $C_{21}$-alkyl, where the sum of the carbon atoms of the $R^i$ and $R^k$ radicals is an integer from 2 to 22;

$R^o$, $R^p$, $R^q$, $R^r$ and $R^s$ in the formula (C.4) are independently selected from the group consisting of $C_1$- to $C_{17}$-alkyl, where the sum of the carbon atoms of the $R^o$, $R^p$, $R^q R^r$ and $R^s$, radicals is an integer from 5 to 21.

Herein, specific examples of the radical C.1 are 1-methylethyl, 1-methylpropyl, 1-methylbutyl, 1-methylpentyl, 1-methylhexyl, 1 methylheptyl, 1-methyloctyl, 1-ethylpropyl, 1-ethylbutyl, 1-ethylpentyl, 1-ethylhexyl, 1 ethylheptyl, 1-ethyloctyl, 1-propylbutyl, 1-propylpentyl, 1-propylhexyl, 1 propylheptyl, 1-propyloctyl, 1-butylpentyl, 1-butylhexyl, 1-butylheptyl, 1-butyloctyl, 1 pentylhexyl, 1 pentylheptyl, 1-pentyloctyl, 1-hexylheptyl, 1-hexyloctyl, 1-heptyloctyl.

Herein, a specific example of the radical C.2 is tert-butyl.

Herein, specific examples of the radical C.3 are isobutyl, 2-methylbutyl, 2-ethylbutyl, 2-ethylpentyl and 2-ethylhexyl.

Herein, a specific example of the radical C.4 is tert-octyl (1,1,3,3-tetramethylbutyl).

In particular, the compound of formula (I.a) is a compound of formula (I-A),

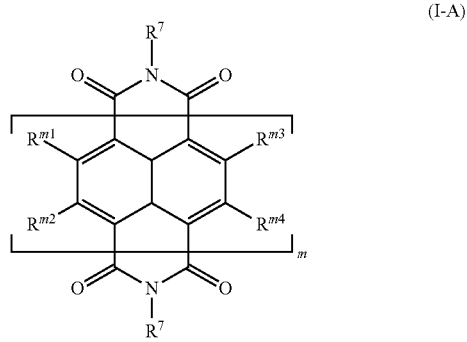

(I-A)

wherein
each $R^7$, independently of one another, is as defined herein above and has preferably one of the meanings mentioned as preferred;
m is 2 or 3; and
$R^{m1}$, $R^{m2}$, $R^{m3}$ and $R^{m4}$ are as defined herein above and have preferably one of the meanings mentioned as preferred.

Compounds (I-A) correspond to compounds (I.a), where $R^5$ and $R^6$ together are a diradical of formula (A.1); and m is 2 or 3.

More particularly, the compound of formula (I-A) is a compound of formulae (I-A.1) or (I-A.2),

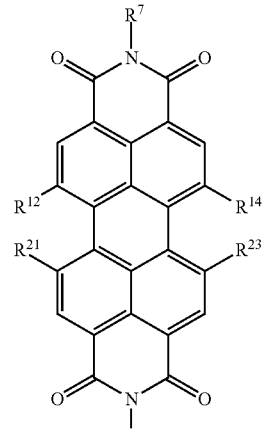

(I-A.1)

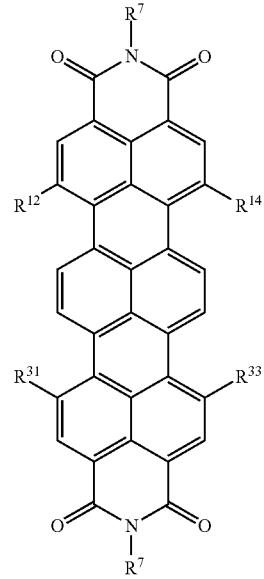

(I-A.2)

wherein
$R^7$ independently of each other is selected from vinyl and 2-propenyl;
at least one of the $R^{12}$, $R^{14}$, $R^{21}$, $R^{23}$, $R^{31}$, $R^{33}$ radicals is phenoxy, which is substituted by one, two or three radicals selected from branched $C_3$-$C_{24}$-alkyl, linear $C_6$-$C_{24}$-alkyl and phenyl-$C_1$-$C_{10}$-alkylene, where the phenyl moiety of phenyl-$C_1$-$C_{10}$-alkylene is unsubstituted or substituted by one, two or three $C_1$-$C_{10}$-alkyl; and
the remaining radicals $R^{12}$, $R^{14}$, $R^{21}$, $R^{23}$, $R^{31}$, $R^{33}$, independently of each other are hydrogen or phenoxy, which is substituted by one, two or three radicals selected from branched $C_3$-$C_{24}$-alkyl, linear $C_6$-$C_{24}$-alkyl and phenyl-$C_1$-$C_{10}$-alkylene, where the phenyl moiety of phenyl-$C_1$-$C_{10}$-alkylene is unsubstituted or substituted by one, two or three $C_1$-$C_{10}$-alkyl.

Particularly preferred are compounds of formula (I-A.1), wherein $R^7$ are 2-propenyl.

Particularly preferred are compounds of formula (I-A.1), wherein two of the radicals (variables) $R^{12}$, $R^{14}$, $R^{21}$ and $R^{23}$ are hydrogen and the remaining radicals $R^{12}$, $R^{14}$, $R^{21}$ and $R^{23}$ are phenoxy, which is substituted by one or two radicals selected from branched $C_3$-$C_{24}$-alkyl and linear $C_6$-$C_{24}$-alkyl, especially branched $C_3$-$C_{24}$-alkyl selected from the group consisting of the radical of formula (C.1), the radical of formula (C.2), the radical of formula (C.3) and the radical of formula (C.3). Also particularly preferred are compounds of formula (I-A.1), wherein each of the radicals $R^{12}$, $R^{14}$, $R^{21}$ and $R^{23}$ is phenoxy, which is substituted by one or two radicals selected from branched $C_3$-$C_{24}$-alkyl or linear $C_6$-$C_{24}$-alkyl, especially branched $C_3$-$C_{24}$-alkyl selected from the group consisting of the radical of formula (C.1), the radical of formula (C.2), the radical of formula (C.3) and the radical of formula (C.3).

Particularly preferred are also compounds of formula (I-A.2), wherein two of the radicals $R^{12}$, $R^{14}$, $R^{31}$ and $R^{33}$ are hydrogen and two of the radicals $R^{12}$, $R^{14}$, $R^{31}$ and $R^{33}$ are phenoxy, which is substituted by one or two radicals selected from branched $C_3$-$C_{24}$-alkyl or linear $C_6$-$C_{24}$-alkyl, especially branched $C_3$-$C_{24}$-alkyl selected from the group consisting of the radical of formula (C.1), the radical of formula (C.2), the radical of formula (C.3) and the radical of formula (C.3). Particularly preferred are also compounds of formula (I-A.2), wherein each of the radicals $R^{12}$, $R^{14}$, $R^{31}$ and $R^{33}$ is phenoxy, which is substituted by one or two radicals selected from branched $C_3$-$C_{24}$-alkyl or linear $C_6$-$C_{24}$-alkyl, especially branched $C_3$-$C_{24}$-alkyl selected from the group consisting of the radical of formula (C.1), the radical of formula (C.2), the radical of formula (C.3) and the radical of formula (C.3).

Particular preference is given to the following compounds of formula (I-A.1):

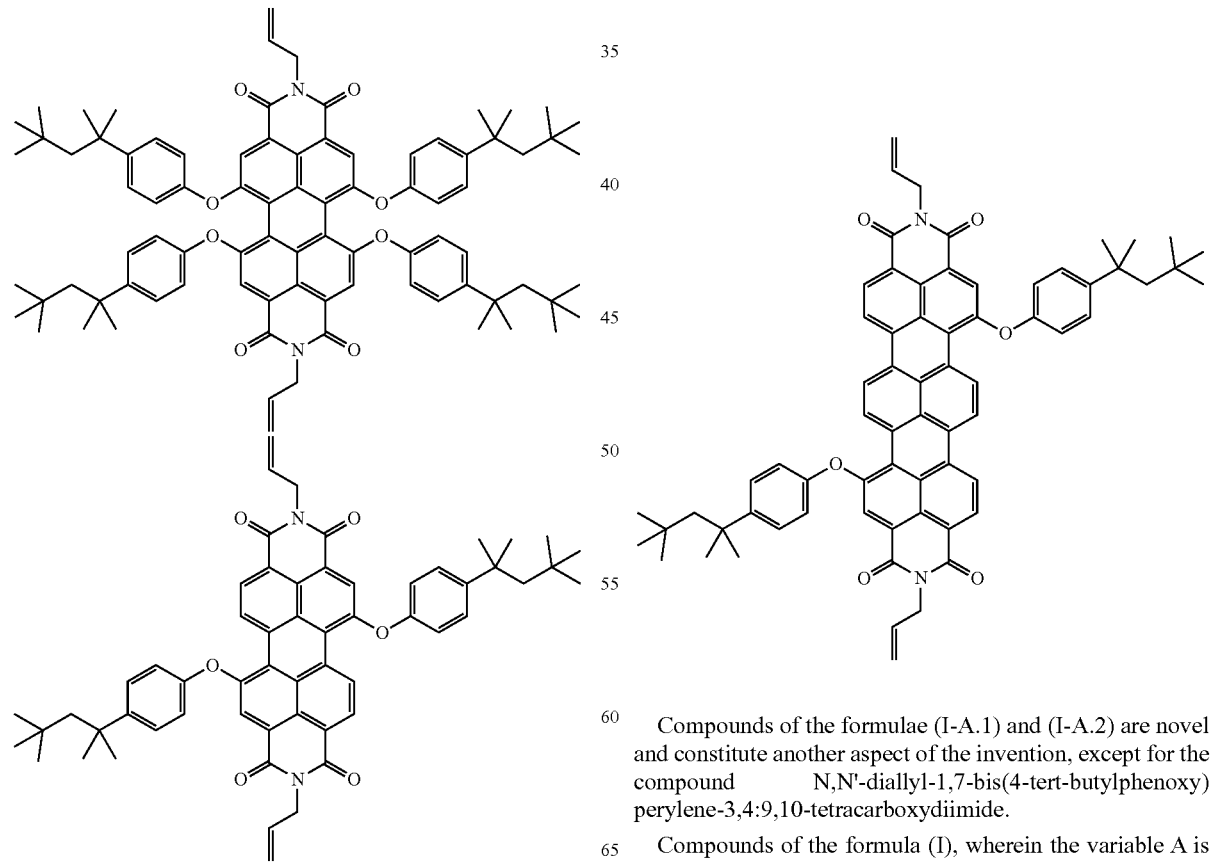

Particular preference is given to the following compounds of formula (I-A.2):

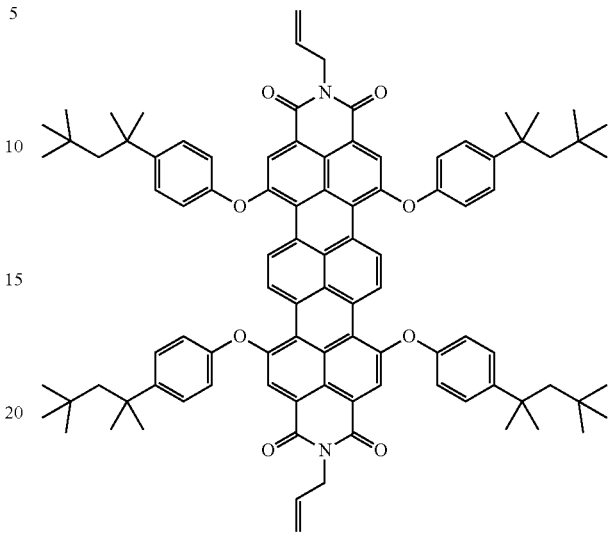

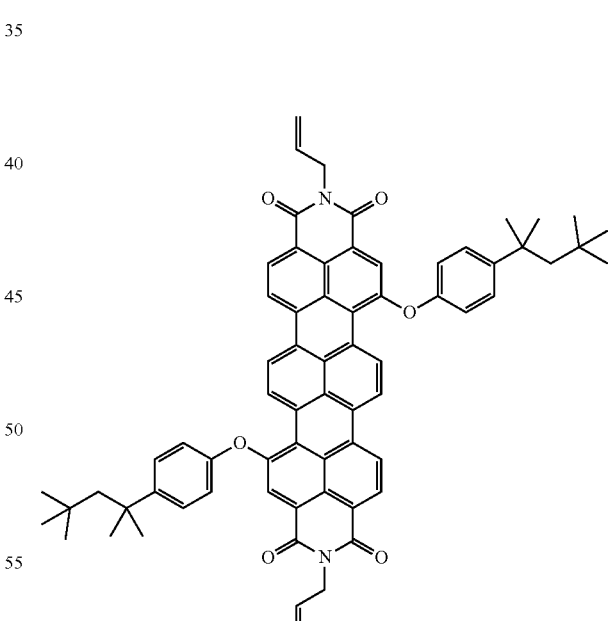

Compounds of the formulae (I-A.1) and (I-A.2) are novel and constitute another aspect of the invention, except for the compound N,N'-diallyl-1,7-bis(4-tert-butylphenoxy)perylene-3,4:9,10-tetracarboxydiimide.

Compounds of the formula (I), wherein the variable A is a diradical of the formula (A.2) have the following formula (I.b),

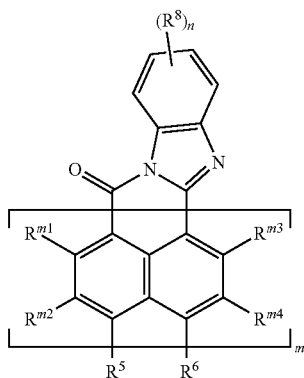

(I.b)

wherein
the indices m and n and the variables $R^5$, $R^6$, $R^8$ are as defined above; and
each $R^{m1}$, $R^{m2}$, $R^{m3}$ and $R^{m4}$, independently of one another, are hydrogen or $C_6$-$C_{14}$-aryloxy, which is substituted by one or more radicals selected from $C_1$-$C_{24}$-alkyl and $C_6$-$C_{14}$-aryl-$C_1$-$C_{10}$-alkylene, where the aryl moiety of $C_6$-$C_{14}$-aryl-$C_1$-$C_{10}$-alkylene is unsubstituted or substituted by one or more $C_1$-$C_{10}$-alkyl and the alkylene moiety of $C_6$-$C_{14}$-aryl-$C_1$-$C_{10}$-alkylene may be interrupted by one or more groups selected from O, S and $NR^a$; and wherein $R^a$ is as defined above.

In particular, the present invention also relates to compounds having the following formula (I-B)

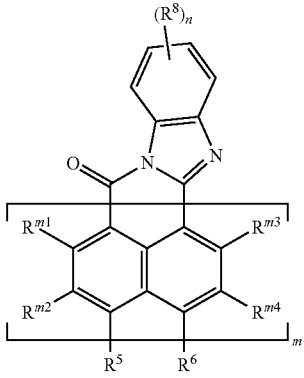

(I-B)

wherein
m is 1 or 2;
n is 1, 2 or 3;
each $R^8$ is as defined above and preferably has one of the preferred meanings;
$R^{m1}$, $R^{m2}$, $R^{m3}$, $R^{m4}$ are as defined above;
$R^5$, $R^6$, independently of each other, are selected from the group consisting of hydrogen and $C_6$-$C_{14}$-aryl, wherein aryl is unsubstituted or substituted with one or two $C_2$-$C_3$-alkenyl groups and 0, 1, 2, 3, 4 or 5 identical or different radicals $R^{5a}$, or
$R^5$ and $R^6$ together are a diradical of the formula (A.2) as defined above.

Compounds (I-B) correspond to compounds (I.b), where m is 1 or 2; and n is 1, 2 or 3.

Preferred are compounds of formula (I-B), wherein at least one of the variables $R^{m1}$, $R^{m2}$, $R^{m3}$, $R^{m4}$ is hydrogen and the remaining variables $R^{m1}$, $R^{m2}$, $R^{m3}$, $R^{m4}$ are $C_6$-$C_{10}$-aryloxy, which is substituted by one or more radicals selected from $C_1$-$C_{24}$-alkyl and $C_6$-$C_{10}$-aryl-$C_1$-$C_{10}$-alkylene, where the aryl moiety of $C_6$-$C_{10}$-aryl-$C_1$-$C_{10}$-alkylene is unsubstituted or substituted by one or more $C_1$-$C_{10}$-alkyl and the alkylene moiety of $C_6$-$C_{10}$-aryl-$C_1$-$C_{10}$-alkylene may be interrupted by one or more, e. g. 1, 2, 3, 4 or more than 4, groups selected from O, S and $NR^a$. In particular, at most two of the variables $R^{m1}$, $R^{m2}$, $R^{m3}$, $R^{m4}$ are different from hydrogen. Even more in particular, all variables $R^{m1}$, $R^{m2}$, $R^{m3}$, $R^{m4}$ are hydrogen.

In particular preferred compounds of the formula (I-B) are selected from compounds of the formulae (I-B.1), (I-B.2) and (I-B.3),

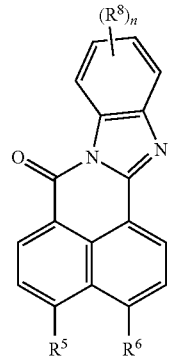

(I-B.1)

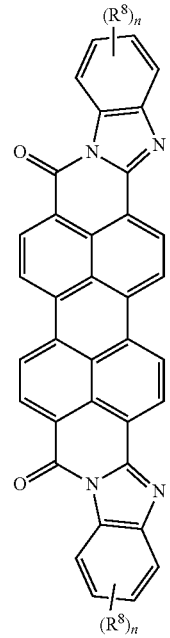

(I-B.2)

-continued (I-B.3)

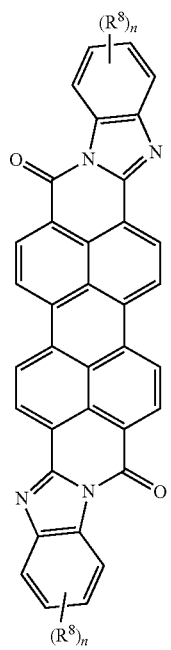

wherein each n independently of each other, is 1, 2 or 3;

$R^5$, $R^6$, if present, independently of each other are hydrogen or phenyl, which is unsubstituted or substituted with one or two $C_2$-$C_3$-alkenyl groups and 0, 1, 2 or 3 radicals $R^{5a}$.

In the context of formula (I-B.1), preferably one of the variables $R^5$ or $R^6$ is phenyl, which is unsubstituted or substituted with one or two $C_2$-$C_3$-alkenyl groups, especially vinyl or 2-propenyl, and the other variable $R^5$ or $R^6$ is hydrogen. Also preferably, both variables $R^5$ and $R^6$ are phenyl which is unsubstituted or substituted with one or two $C_2$-$C_3$-alkenyl groups. In the context of formula (I-B.1), $R^8$ preferably is phenyl or phenyl which is substituted with one or two $C_2$-$C_3$-alkenyl groups, especially vinyl or 2-propenyl, and 0, 1 or 2 radicals $R^{8a}$, where $R^{8a}$ is as defined herein.

In the context of compounds of formulae (I-B.2) and (I-B.3), each $R^8$ preferably is phenyl which is substituted with one or two $C_2$-$C_3$-alkenyl groups, especially vinyl or 2-propenyl, and 0, 1 or 2 radicals $R^{8a}$, where $R^{8a}$ is as defined herein.

Particular preference is given to the following compounds of formula (I-B):

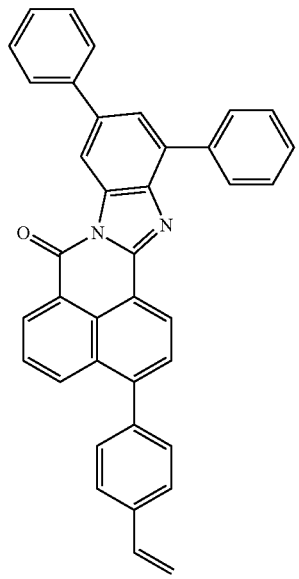

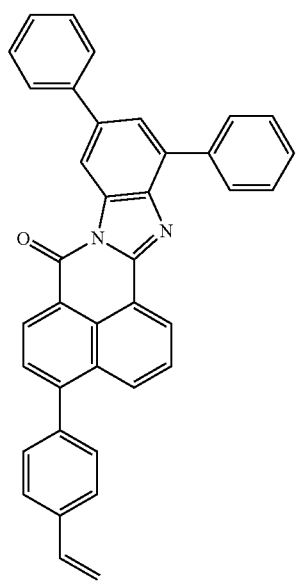

23
-continued
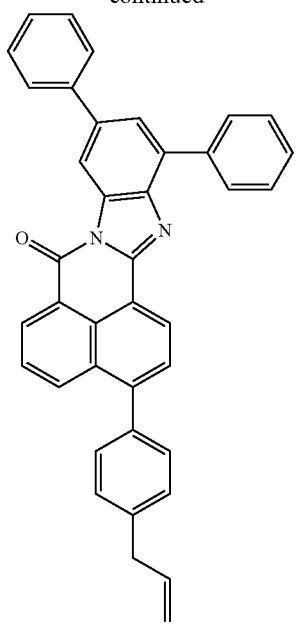
24
-continued
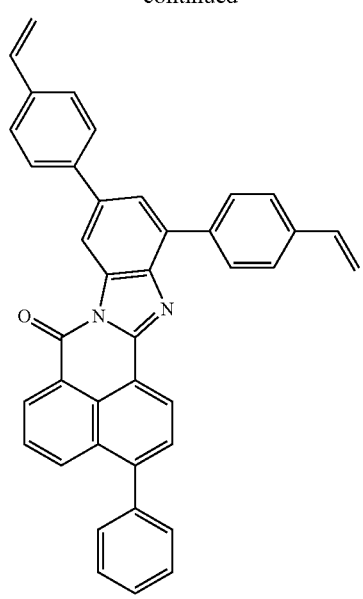
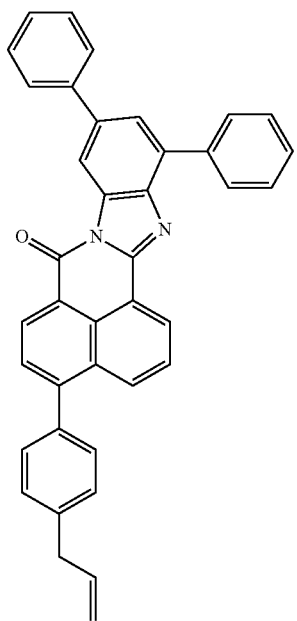
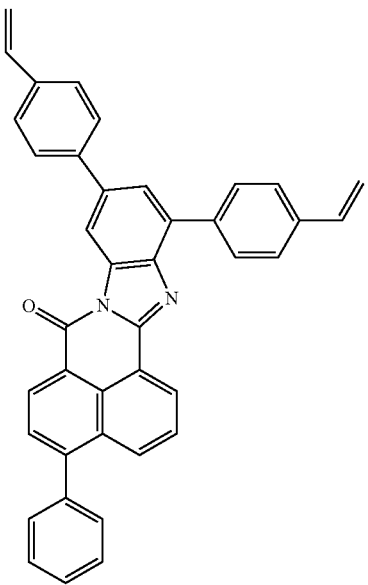

25
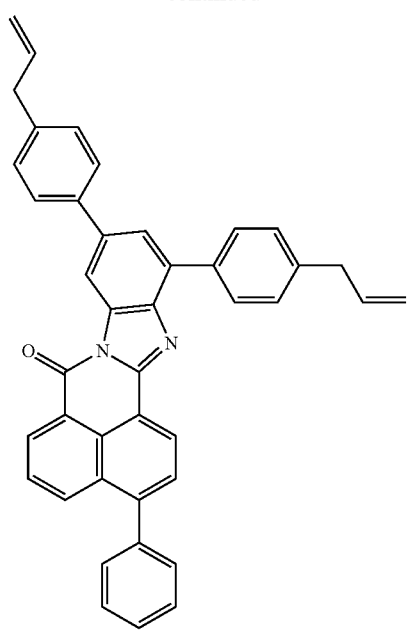
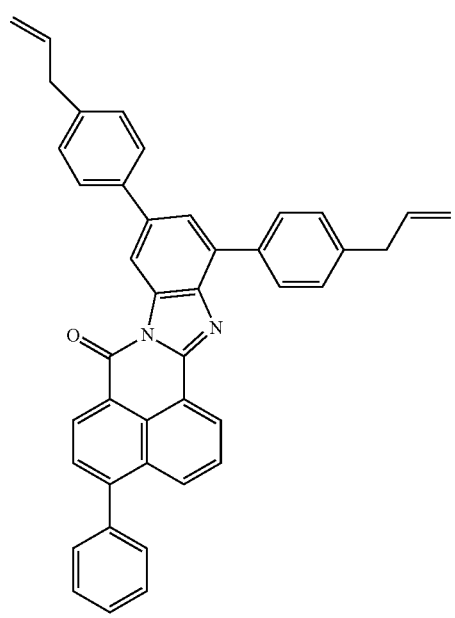
26
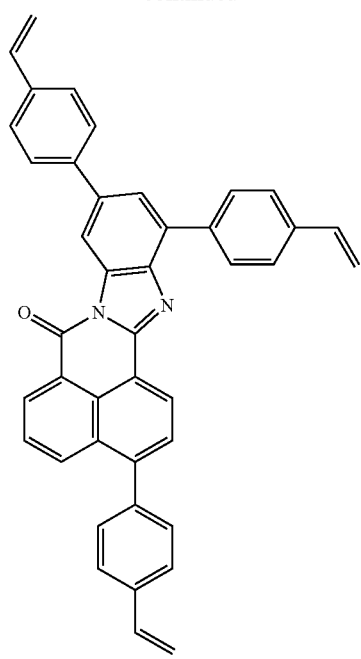
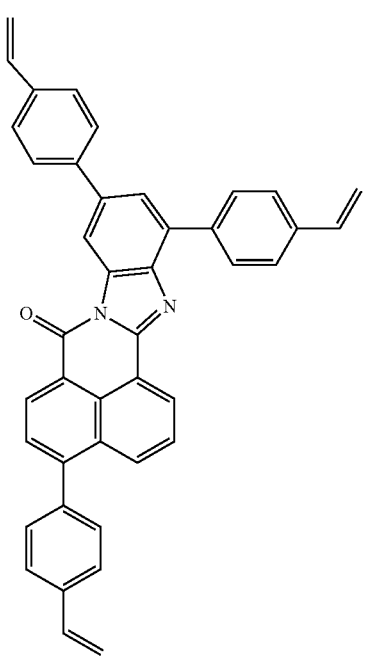

-continued

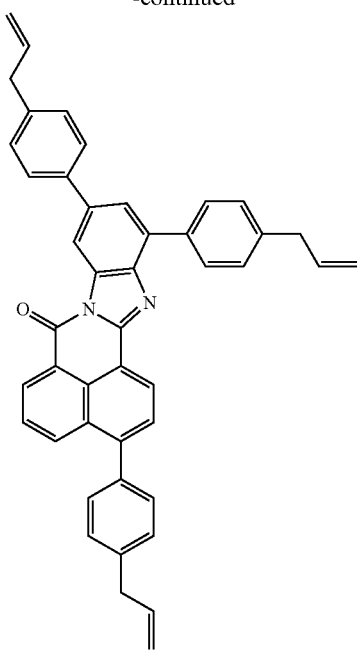

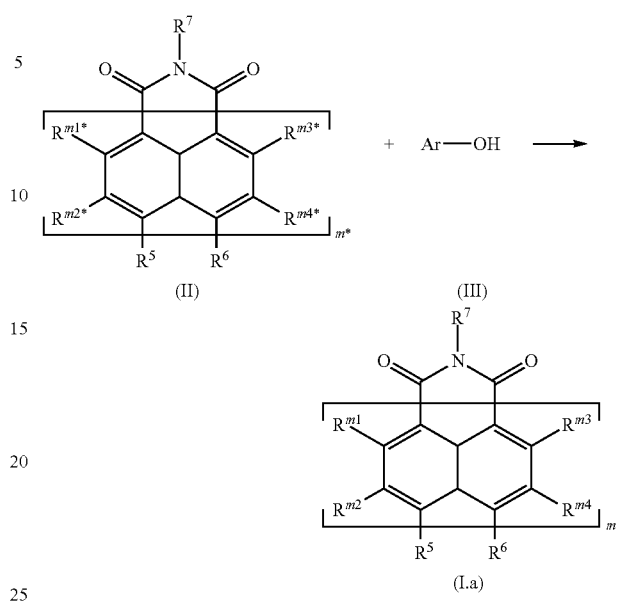

Scheme 1

(II)     (III)

(I.a)

In Scheme 1, m* is 1, 2 or 3; each $R^{m1*}$, $R^{m2*}$, $R^{m3*}$ and $R^{m4*}$, independently of one another, are bromine, chlorine or has one of the meanings given for $R^{m1}$, $R^{m2}$, $R^{m3}$ and $R^{m4}$, where at least one of the variables $R^{m1*}$, $R^{m2*}$, $R^{m3*}$ and $R^{m4*}$, in the compounds of the formula (II), is bromine or chlorine; and Ar is $C_6$-$C_{14}$-aryloxy, which is substituted by one or more radicals selected from $C_1$-$C_{24}$-alkyl and $C_6$-$C_{14}$-aryl-$C_1$-$C_{10}$-alkylene, where the aryl moiety of $C_6$-$C_{14}$-aryl-$C_1$-$C_{10}$-alkylene is unsubstituted or substituted by one or more $C_1$-$C_{10}$-alkyl and the alkylene moiety of $C_6$-$C_{14}$-aryl-$C_1$-$C_{10}$-alkylene may be interrupted by one or more groups selected from O, S and $NR^a$.

The reaction is usually carried out in the presence of a base. Suitable bases are in particular inorganic alkali metal or alkaline earth metal bases, the alkali metal bases being particularly suitable. Examples of inorganic bases are the carbonates and hydrogencarbonates, hydroxides, hydrides and amides of alkali metals and alkaline earth metals. Preferred bases are the carbonates and hydrogencarbonates, particular preference being given to the carbonates. Preferred alkali metals are lithium, sodium, potassium and cesium; particularly suitable alkaline earth metals are magnesium and calcium. It will be appreciated that it is also possible to use base mixtures. Very particularly preferred bases are lithium carbonate, sodium carbonate, potassium carbonate and cesium carbonate.

The reaction is usually carried out in the presence of a polar, aprotic solvent. Suitable solvents are especially aliphatic carboxamides, preferably N,N-di-$C_1$-$C_4$-alkyl-$C_1$-$C_4$-carboxamides, lactams such as dimethylformamide, diethylformamide, dimethylacetamide, dimethylbutyramide and N-methyl-2-pyrrolidone (NMP), nitriles such as acetonitrile. It is also possible to use mixtures of polar, aprotic solvents. Particular preference is given to NMP.

The reaction temperature is generally within the range from room temperature to the boiling point of the solvent, preferably room temperature to 160° C.

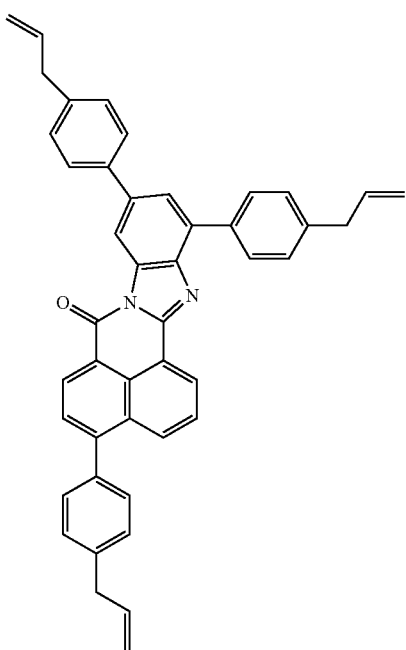

Compounds of formulae (I-B), (I-B.1), (I-B.2) and (I-B.3) are novel and constitute another aspect of the invention.

The compounds of formula (I) can be prepared by standard methods of organic chemistry, e.g. by the methods described in the schemes and the experimental part below. The substituents, variables and indices used in the schemes are as defined above for the compounds of formula (I), if not specified otherwise.

The compounds of formula (I.a) can be prepared analogous to Scheme 1 below by treating a rylenecarboximide of formula (II) with a hydroxy aromatic compound of formula (III):

The rylenecarboximides of formula (II) can be prepared by imidating the correspondingly substituted anhydrides (IV) as outlined in Scheme 2.

Scheme 2

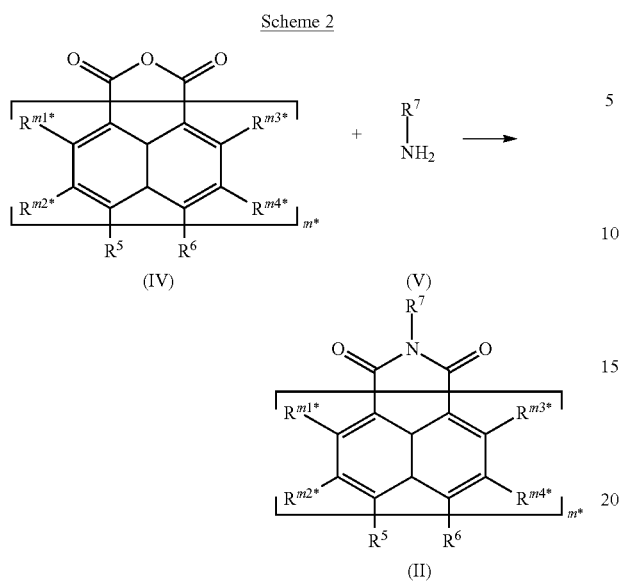

The imidation of carboxylic anhydride groups is known in principle. Preference is given to reacting the anhydride of formula (IV) with the primary amine of formula (V) in the presence of an imidation catalyst. Suitable imidation catalysts are Lewis and Brønsted acids, for example organic and inorganic acids, e.g. formic acid, acetic acid, propionic acid and phosphoric acid. Suitable Lewis acids are in particular zinc, copper and iron salts, and it is also possible to use the oxides in the case of copper. Preference is given to the zinc and copper compounds, particular preference being given to the zinc compounds. Examples of suitable Lewis acids are zinc acetate, zinc propionate, copper(I) oxide, copper(II) oxide, copper(I) chloride, copper(I) acetate and iron(III) chloride, very particular preference being given to zinc acetate.

The compounds of formula (I.b), where $R^5$ and $R^6$ are selected from hydrogen and optionally substituted $C_6$-$C_{14}$-aryl can be prepared analogous to Scheme 3 below by a cross-coupling in the presence of a transition metal catalyst starting from a compound of formula (VI) and an organometallic compound of the formula (VII):

Scheme 3

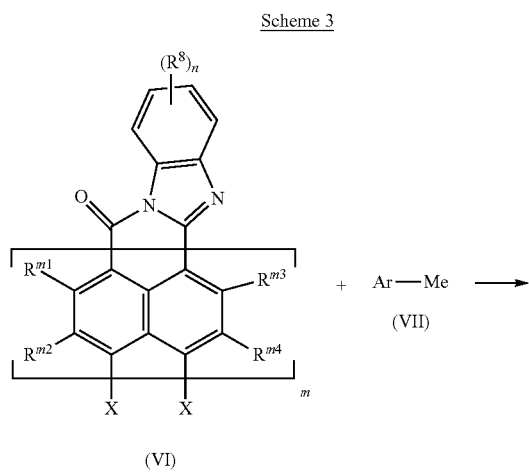

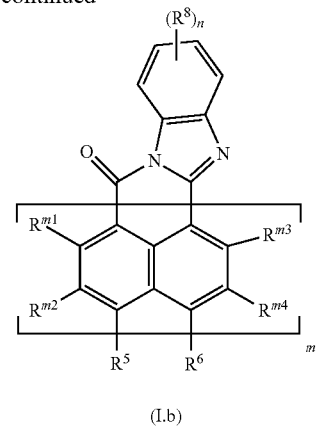

In the compound of formula (VI), X is chlorine, bromine, hydrogen or $C_6$-$C_{14}$-aryl, wherein aryl is unsubstituted or substituted with one or two $C_2$-$C_3$-alkenyl groups and 0, 1, 2, 3, 4 or 5 identical or different radicals $R^{5a}$, where at least one of the variables X is chlorine or bromine.

In the compounds of formula (VII), Ar is $C_6$-$C_{14}$-aryl, wherein aryl is unsubstituted or substituted with one or two $C_2$-$C_3$-alkenyl groups and 0, 1, 2, 3, 4 or 5 identical or different radicals $R^{5a}$, and Me is $B(OH)_2$, $B(OR')(OR'')$, Zn—R''' or $Sn(R^*)_3$, in which R' and R'' are each independently hydrogen, $C_1$-$C_{30}$-alkyl, $C_5$-$C_8$-cycloalkyl, or $C_6$-$C_{14}$-aryl, or R' and R'' together are $C_2$-$C_4$-alkylene which optionally bears 1, 2, 3, 4, 5, 6, 7 or 8 substituents selected from $C_1$-$C_4$-alkyl, $C_5$-$C_5$-cycloalkyl, and $C_6$-$C_{14}$-aryl, R''' is $C_1$-$C_8$-alkyl or phenyl and R* is $C_1$-$C_8$-alkyl or phenyl.

Preference is given to effecting the reaction in the presence of catalytically active amounts of a transition metal of transition group VIII of the Periodic Table (group 10 according to IUPAC), for example nickel, palladium or platinum, especially in the presence of a palladium catalyst. Suitable catalysts are, for example, palladium-phosphine complexes such as tetrakis(triphenylphosphine)palladium(0), $PdCl_2$(o-tolyl$_3$P)$_2$, bis(triphenylphosphine)palladium(II) chloride, the [1,1'-bis(diphenyl-phosphino)ferrocene]palladium(II) chloride-dichloromethane complex, bis[1,2-bis(diphenylphosphino)ethane]palladium(0) and [1,4-bis(diphenylphosphino)-butane]palladium(II) chloride, palladium on activated carbon in the presence of phosphine compounds, and palladium(II) compounds such as palladium(II) chloride or bis(acetonitrile)palladium(II) chloride in the presence of phosphine compounds such as triphenylphosphine, 1,1'-bis(diphenylphosphino)ferrocene, 1,2-bis(diphenylphosphino)-ethane, 1,3-bis(diphenylphosphino)propane and 1,4-bis(diphenylphosphino)butane.

Especially suitable organometallic compounds (VII) are an appropriately substituted arylboronic acid and arylboronic esters. The reaction is effected under the conditions of a Suzuki coupling, as known, for example, from Suzuki et al., Chem. Rev., 1995, 95, 2457-2483 and the literature cited therein. The Suzuki coupling is effected under basic conditions. Suitable bases are alkali metal carbonates and alkali metal hydrogencarbonates such as sodium carbonate, potassium carbonate, cesium carbonate, sodium hydrogencarbonate, alkaline earth metal carbonates and alkaline earth metal hydrogencarbonates such as magnesium carbonate or magnesium hydrogencarbonate, or tertiary amines such as triethylamine, trimethylamine, triisopropylamine or N-ethyl-N-diisopropylamine.

Compounds of formula (VI) are known from WO 2012/168395 or can be prepared in analogy to methods described therein. Arylboronic acid and arylboronic esters of formula VII can be prepared according to standard methods or are commercially available.

The compounds of formula (I.b), where $R^5$ and $R^6$ together are a diradical of the formula (A.2) can be prepared analogous to Scheme 4 by reacting a dianhydride of the formula (VIII) with an amine of the formula IX to give a mixture of the syn and anti compounds of formula (I.b)

Scheme 4

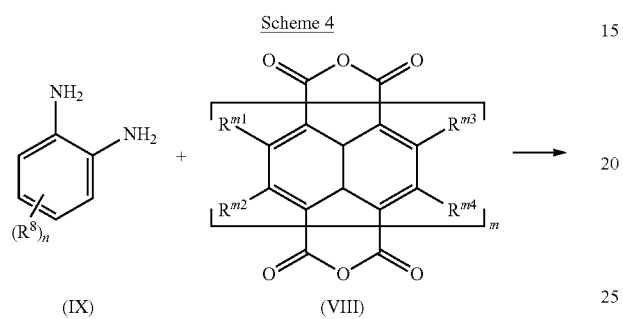

(IX)   (VIII)

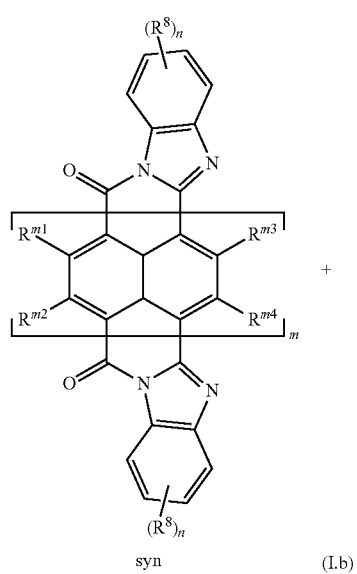

syn   (I.b)

-continued

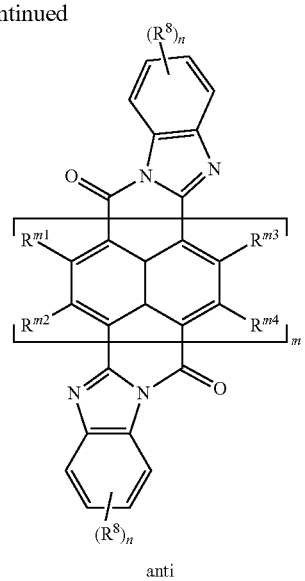

anti

The reaction can be performed in analogy to the method described in Scheme 2. Compounds of the formula (IX) can be prepared by treating a halogenated 6-nitroaniline with an appropriate substituted phenylboronic acid or ester in the sense of a Suzuki coupling followed by reduction of the nitro group to an amino group.

A common feature of all compounds of formulae (I), (I.a) and (I.b) is that they have at least one curable functional group, i.e. at least one $C_2$-$C_3$-alkenyl group, which enables hydrosilylation reaction with an addition-curable silicone resin. The hydrosilylation reaction allows that the compounds of formula (I) are covalently bonded to the siloxane backbone.

The curable silicone resin according to the invention comprises as further essential component a curable silicone resin mixture. The curable silicone resin mixture comprises a curable organopolysiloxane and a hydrosilylation catalyst. The curable organopolysiloxane is a hydride functional polymer, i.e. the organopolysiloxane contains silicon bonded hydrogen atoms which can undergo a hydrosilylation reaction in the presence of the hydrosilylation catalyst.

In a first embodiment, the curable silicone resin comprises the hydrosilylation catalyst and an organopolysiloxane containing at least one, e.g. two, three or more hydrogen atoms bonded to a silicon atom per molecule, i.e., the organopolysiloxane contains hydrosilyl groups (Si—H) groups. The hydrogen atoms may be located at the termini of the molecule. Besides hydrogen atoms, the organopolysiloxane contains pendant groups (side groups). Suitable pendant groups are $C_1$-$C_6$-alkyl groups (e.g. methyl) and $C_6$-$C_{10}$-aryl groups which are unsubstituted or substituted by $C_1$-$C_{10}$-alkyl (e.g., phenyl, naphthyl, tolyl). The curable organopolysiloxane can have a linear, branched, cyclic or three-dimensional network structure. Specific examples are dimethylsiloxane/methylhydrogensiloxane copolymers and organopolysiloxane comprising silicon bonded diphenyl, dimethyl and phenylmethyl units besides Si—H units.

In a second embodiment, the curable silicone resin mixture comprises a hydrosilylation catalyst, an organopolysiloxane C.1 having at least two silicon bonded alkenyl groups per molecule and an organopolysiloxane C.2 having at least two hydrogen atoms bonded to a silicon atom per molecule. The organopolysiloxane C.1 may be linear, branched or cyclic. When the organopolysiloxane C.1 has a linear structure, the alkenyl groups may be bonded on a terminal silicon atom. According to a preferred embodiment, the curable silicon resin mixture comprises a linear organopolysiloxane C.1a having at least two silicon bonded alkenyl groups per molecule and a branched organopolysiloxane C.1b having at least one silicon bonded alkenyl group. Each silicon bonded alkenyl group preferably has 2 to 6 carbon atoms. The alkenyl groups are exemplified by vinyl, 2-propenyl (allyl), butenyl, pentenyl, and hexenyl. In particular, vinyl and 2-propenyl are preferred, and vinyl is even more preferred. The branched organopolysiloxane C.1b having at least one silicon bonded alkenyl group, if present, is contained in an amount necessary for a weight ratio of from 1:99 to 99:1 relative to the linear organopolysiloxane C.1a having at least two silicon bonded alkenyl groups per molecule.

The siloxane backbone of the organopolysiloxane C.1, C.1a, C.1b usually has pendants groups. Suitable pendants groups are exemplified by $C_1$-$C_{10}$-alkyl (e.g. methyl, ethyl, n-propyl, n-butyl, n-pentyl), halogenated $C_1$-$C_{10}$-alkyl (e.g. chloromethyl, 3-chloropropyl, 3,3,3-trifluoropropyl), phenyl, naphthyl, $C_6$-$C_{10}$-aryl which is substituted by $C_1$-$C_{10}$-alkyl (e.g. tolyl, xylyl), $C_6$-$C_{10}$-aryl-$C_1$-$C_{10}$-alkylene (e.g. benzyl, phenethyl, phenylpropyl). In particular, methyl and phenyl groups are attached to the siloxane backbone. Likewise in particular, all pendant groups are methyl groups.

The organopolysiloxane C.2 may be linear, branched or cyclic. When the organopolysiloxane has a linear structure, the Si—H groups may be at the terminal end of the molecular chain. In addition, the siloxane backbone of C.2 usually has pendant groups. Examples include $C_1$-$C_{10}$-alkyl (e.g. methyl, ethyl, n-propyl, n-butyl, n-pentyl), halogenated $C_1$-$C_{10}$-alkyl (e.g. chloromethyl, 3-chloropropyl, 3,3,3-trifluoropropyl), phenyl, naphthyl, $C_6$-$C_{10}$-aryl which is substituted by $C_1$-$C_{10}$-alkyl (e.g. tolyl, xylyl), $C_6$-$C_{10}$-aryl-$C_1$-$C_{10}$-alkylene (e.g. benzyl, phenethyl, phenylpropyl). In particular, methyl and phenyl groups are attached to the siloxane backbone. Likewise in particular, all pendant groups are methyl groups.

The amount of Si—H groups provided by the organopolysiloxane C.2 preferably is in the range from 0.1 to 10 mol, preferably in the range of from 0.1 to 5 mol per 1 mol of the alkenyl groups contained in the organopolysiloxane compound C.1 and, organopolysiloxane compounds C.1a and C.1b, respectively.

The hydrosilylation catalyst may be a conventional one. Suitable hydrosilylation catalysts are platinum catalysts, rhodium catalysts, and palladium catalysts, with platinum catalysts being preferable. The hydrosilylation catalyst is often a complex of platinum in ethanol, xylene, divinylsiloxanes or cyclic vinylsiloxanes. Suitable hydrosilylation catalysts include the Karstedt's catalyst and platinum carbonyl cyclovinylmethylsiloxane.

The (addition-curable) silicone resin mixture may be of one component or two component type. Preference is given to two component type for its easy availability and better storage suitability. In a two part component system, part A usually comprises the hydrosilylation catalyst and the organopolysiloxane having at least two silicon bonded alkenyl groups and part B comprises the organopolysiloxane having at least two hydrogen atoms each bonded to a silicon atom.

Suitable addition-curable silicone resin mixture are described in US 2016/340510; U.S. Pat. No. 9,048,406; US2014/0021502; US 2014/131740; and US 2007/0112147, especially paragraph [0031] to paragraph [0038] of US 2007/0112147.

Examples of commercially available two-component (addition-curable) silicone resin mixtures include Dow Corning® OE-6630 (available from Dow Corning, USA) and KJR9022E (available from Shin-Etsu Chemical, Japan).

The addition-curable silicone resin mixture may comprise additives. Suitable additives are inorganic fillers, antioxidants, inorganic phosphors, organic fluorescent dyes different from compounds of formula (I), lubricants, heat stabilizer, light stabilizer, dispersants, antistatic agents, antifoamers, solvents, anti-aging agents, radical inhibitors, polymerization inhibitors, flame retardants, scattering bodies and adhesion-imparting agent.

The inorganic fillers may be fine-particle fillers which do not deteriorate optical properties. Examples thereof include alumina, aluminum hydroxide, fused silica, crystalline silica, ultrafine amorphous silica, hydrophobic ultrafine silica, talc, calcium carbonate, and barium sulfate.

Examples of the inorganic phosphors include yttrium aluminum garnet (YAG) phosphors, red light emitting phosphors, blue light emitting phosphors and green light emitting phosphors.

Examples of scattering particles include inorganic white pigments, for example titanium dioxide, barium sulphate, lithopone, zinc oxide, zinc sulphide, zirconia, alumina powder, calcium carbonate with a mean particle size to DIN 13320 of 0.001 to 10 μm, preferably 0.01 to 1 μm, more preferably 0.15 to 0.4 μm, especially scattering bodies based on $TiO_2$. The curable silicone resin composition according to the invention preferably includes at least one light scattering agent as defined herein above.

The amount of the compound of formula (I) is usually in the range from 0.0001 to 1% by weight, based on the total amount of the components C.1 and C.2 and, C.1a, C.1b and C.2, respectively.

According to a preferred embodiment, the curable silicon resin composition does not contain any other curable polymer. According to this embodiment, the curable silicone resin composition includes as curable resin exclusively the curable silicone resin mixture described above.

The curable silicone resin composition according to the invention is advantageously cured by heating. Preference is given to curing by heating at 100° C. or higher, preferably 120° C. to 200° C., still more preferably 120° C. to 180° C.

The curable silicone resin composition is obtainable by blending the at least one compound of formula (I), the curable silicone resin mixture, if present at least one light scattering agent and optionally (an) additive(s) as described above.

The curable silicon resin composition affords transparent cured products suitable for use in LED devices. Especially the covalently incorporated compound of formula (I) has a long lifetime when compared to the lifetime of fluorescent dyes not covalently incorporated into a polymer matrix.

The present invention also relates to a polymer comprising in copolymerized form:
(a) at least one compound of formula (I) as defined above; and
(b) an organopolysiloxane C.

The polymer of the invention more preferably comprises in copolymerized form at least one compound of formula (I-A). Likewise preferably, the polymer of the invention comprises in copolymerized form at least one compound of formula (I-B). More preferably, the polymer of the invention comprises at least one compound of formula (I-A.1). Likewise more preferably, the polymer of the invention comprises in copolymerized form at least one compound of formula (I-A.2). Likewise more preferably, the polymer of the invention comprises in copolymerized form at least one compound of formula (I-B.1). Likewise more preferably, the polymer of the invention comprises in copolymerized form at least one compound of formula (I-B.2). Likewise more preferably, the polymer of the invention comprises in copolymerized form at least one compound of formula (I-B.3). Likewise more preferably, the polymer of the invention comprises in copolymerized form at least one compound of formulae (I-B.2) and (I-B.3).

The organopolysiloxane C is a hydride functional polymer, i.e. the organopolysiloxane C contains silicon bonded hydrogen atoms which can undergo a hydrosilylation reaction with a $C_2$-$C_3$-alkenyl-substituted rylene imide compound of formula I as defined above in the presence of a hydrosilylation catalyst.

The polymer according to the invention preferably comprises in copolymerized form
(i) an organopolysiloxane C.1 having at least two silicon-bonded $C_2$-$C_6$-alkenyl groups per molecule;
(ii) an organopolysiloxane C.2 having at least two silicon-bonded hydrogen atoms per molecule; and
(iii) at least compound of formula I as defined herein.

Examples of the organopolysiloxane C.1 are the same as given above. Suitable organopolysiloxanes C.2 are the same as given above.

In a first specific embodiment, the organopolysiloxane C is a copolymer of
(i) an organopolysiloxane C.1 having at least two silicon-bonded $C_2$-$C_6$-alkenyl groups and at least one silicon-bonded $C_1$-$C_6$-alkyl group; and
(ii) an organopolysiloxane C.2 having at least two silicon bonded hydrogen atoms and at least one silicon-bonded $C_1$-$C_6$-alkyl group.

In a second specific embodiment, the organopolysiloxane C is a copolymer of
(i) a linear organopolysiloxane C.1a having at least two silicon-bonded $C_2$-$C_6$-alkenyl groups and at least one silicon-bonded $C_1$-$C_6$-alkyl group;
(ii) an organopolysiloxane C.2 having at least two silicon bonded hydrogen atoms and at least one silicon-bonded $C_1$-$C_6$-alkyl group; and
(iii) optionally a branched organopolysiloxane C.1b having at least one silicon-bonded $C_2$-$C_6$-alkenyl group and at least one silicon-bonded $C_1$-$C_6$-alkyl group.

According to the first and second specific embodiment, the backbone of the organopolysiloxane C.1, or the backbone of C.1a and C.1b contains alkyl groups such as methyl but no aryl groups such as phenyl groups as pendant groups. Although there is no specific regard to the ratio of the total sum of alkenyl groups to the total sum of alkyl groups, the ratio of alkyl groups to alkenyl groups preferably is at least 20:1, more preferably at least 30:1. According to the first and second specific embodiment, each alkenyl group preferably is a vinyl group. Likewise, each alkenyl group preferably is an allyl group.

Preferred examples of organopolysiloxane C.2 have at least two silicon bonded hydrogen atoms and at least one silicon-bonded methyl group. Although there is no specific regard to the ratio of alkyl groups to silicon-bonded hydrogen atoms, the ratio of alkyl groups to hydride groups preferably is at least 2:1, more preferably at least 3:1. In particular, the organopolysiloxane C.2 according to the first and second specific embodiment does not comprise any aryl group.

In a third specific embodiment, the organopolysiloxane C comprises in polymerized form
(i) an organopolysiloxane C.1 having at least two silicon-bonded $C_2$-$C_6$-alkenyl groups, at least one silicon-bonded $C_1$-$C_6$-alkyl group and at least one silicon bonded $C_6$-$C_{10}$-aryl group, which is unsubstituted or substituted by methyl, per molecule;
(ii) a organopolysiloxane C.2 having at least two silicon bonded hydrogen atoms, at least one silicon-bonded $C_1$-$C_6$-alkyl group and at least one silicon bonded $C_6$-$C_{10}$-aryl group, which is unsubstituted or substituted by methyl, per molecule.

In a fourth specific embodiment, the organopolysiloxane C is a copolymer of
(i) a linear organopolysiloxane C.1a having at least two silicon-bonded $C_2$-$C_6$-alkenyl groups, at least one silicon-bonded $C_1$-$C_6$-alkyl group and at least one silicon bonded $C_6$-$C_{10}$-aryl group, which is unsubstituted or substituted by methyl, per molecule;
(ii) an organopolysiloxane C.2 having at least two silicon bonded hydrogen atoms, at least one silicon-bonded $C_1$-$C_6$-alkyl group and at least one silicon bonded $C_6$-$C_{10}$-aryl group, which is unsubstituted or substituted by methyl, per molecule; and
(iii) optionally a branched organopolysiloxane C.1b having at least one silicon-bonded $C_2$-$C_6$-alkenyl group, and at least one silicon-bonded $C_6$-$C_{10}$-aryl group, which is unsubstituted or substituted by methyl, per molecule According to the third and fourth specific embodiment, the backbone of the organopolysiloxane C.1 or the backbone of C.1a and C.1b contains alkyl groups such as methyl and optionally substituted $C_6$-$C_{10}$-aryl groups such as phenyl or tolyl as pendant groups. Although there is no specific regard to the ratio of the sum of alkyl groups to the sum of alkenyl groups, the ratio of alkyl groups to alkenyl groups preferably is at least 8:1, more preferably at least 10:1. Although there is no specific regard to the ratio of alkyl groups to optionally substituted $C_6$-$C_{10}$-aryl groups, the ratio of alkyl groups to the optionally substituted $C_6$-$C_{10}$-aryl groups preferably is at least 1:1, more preferably at least 1.05:1.

Examples for preferred organopolysiloxane C.2 include compounds having at least two silicon bonded hydrogen atoms, at least one silicon-bonded methyl group and at least one silicon-bonded phenyl group or compounds having at least two silicon bonded hydrogen atoms, at least one silicon-bonded methyl group and at least one silicon-bonded tolyl group. Although there is no specific regard to the ratio of alkyl groups to silicon-bonded hydrogen atoms, the ratio of alkyl groups to hydride groups is preferably at least 2:1. Although there is no specific regard to the ratio of alkyl groups to silicon-bonded $C_6$-$C_{10}$-aryl groups, the ratio of alkyl groups to $C_6$-$C_{10}$-aryl groups is at least 2:1.

Examples of a commercially available two components organpoylsiloxane mixtures are Dow Corning® OE-6630 (available from Dow Corning, USA) and KJR9022E (available from Shin-Etsu Chemical, Japan).

The polymer according to the invention comprises the at least one copolymerized compound of formula I in an amount of 0.0001 to 1% by weight, based on the amount of the organopolysiloxane C.

The polymer according to the invention is preferably used with LED devices for the purposes of protection, encapsulation and wavelength conversion or adjustment, and lens formation of LED devices.

The polymer according to the invention is prepared via a hydrosilylation reaction. As to suitable hydrosilylation catalyst, reference is made to what is said above. The polymer according to the invention may also comprise unreacted monomers. In addition, the polymer optionally comprises at least one component selected from inorganic phosphors, organic fluorescent compounds different from compound of formula I, scattering bodies, filler, heat stabilizer, antioxidants, lubricants, light stabilizer, dispersants, antistatic agents, antifoamers, solvents, anti-aging agents, radical inhibitors, polymerization inhibitors, flame retardants, and adhesion-imparting agents. As regards the optional components, reference is made to what is said above in the context of the curable silicone resin composition.

Incorporation of the compound of formula (I) into an addition curable organopolysiloxane via hydrosilylation reaction significantly increases the stability of the organic fluorescent compound of formula (I) against blue LED light compared to structural related prior art compounds. This is attributed to the chemical bonding of the compound of the formula (I) to the organopolysiloxane backbone. This crosslink network is in particular advantageous for opto-electronic applications since the fluorescence quantum yield of the organic fluorescent compound is kept at high level and the emission maximum is shifted at most in the range of a few nanometers compared to the unmodified organic fluorescent compound.

The present invention also relates to the use of the polymer according to the invention in the manufacture of an LED device. In particular, the polymer according to the invention can be used as encapsulating material for phosphor conversion. The polymer according to the invention can be used for converting light emitted from a blue LED with a center wavelength of emission between 400 nm and 480 nm into light of a second, longer wavelength, for converting light emitted from a white LED, said white LED having a correlated color temperature between 3 000 K and 20 000 K to provide white light having a lower correlated color temperature, for transmitting data or for emitting electromagnetic radiation in the visible spectral range.

Thus, the present invention also relates to a lighting device, comprising at least one blue LED with a center wavelength of emission between 400 nm and 480 nm and a polymer as defined above, wherein the polymer is disposed in front of the LED in its emission direction and where the polymer is not spaced from the LED. The lighting device is characterized in that the at least one LED is coated with the cured product of the above-mentioned curable organopolysiloxane containing the compound of formula (I), preferably with the cured product of the curable organopolysiloxane C containing 0.0001 to 1% by weight of the compound of formula (I), based on the amount of the organopolysiloxane. It may be advantageous to seal the coated LED element.

The invention is illustrated in detail by the examples described hereinafter. At the same time, the examples should not be regarded as a restriction of the invention. In particular, the fluorescent compounds of formula I and the curable organopolysiloxane composition of the invention will be further described in more detail with reference to practical examples. The preparation of the compounds according to the invention is illustrated by examples; however, the subject matter of the present invention is not limited to the examples given.

EXAMPLES

I. Preparation of $C_2$-$C_3$-Alkenyl Substituted Dyes According to the Invention Example I: Preparation of

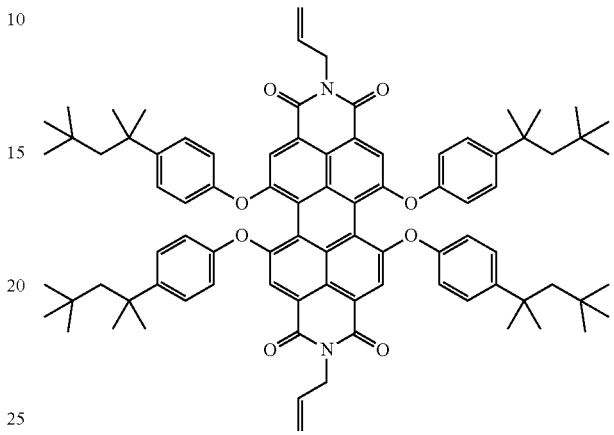

I.1 Preparation of N,N'-diallyl-1,6,7,12-tetrachloroperylene-3,4:9,10-tetracarboxylic Acid Diimide A mixture of 2.65 g (5 mmol) of 1,6,7,12-tetrachloroperylene-3,4;9,10-tetracarboxylic acid dianhydride, 2.75 g (15 mmol) of zinc acetate, 30 mL of N-methylpyrrolidone and 1.52 g (26 mmol) of allylamine were heated to 100° C. for 23 hours. The reaction mixture was cooled to room temperature and 250 mL of brine were added. The formed solid was isolated by filtration, washed with water and dried at 70° C. under reduced pressure. The product was used without further purification for the next step.

Rf (toluene:acetone 100:1)=0.45.

I.2 Preparation of

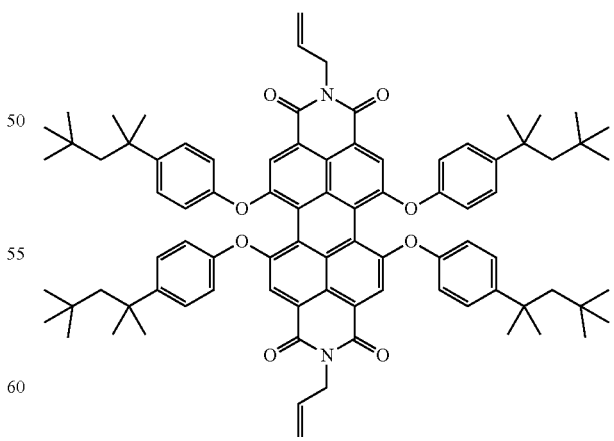

A mixture of 3.04 g (5 mmol) of the compound from example I.1, 70 mL of N-methylpyrrolidone, 5.16 g (25 mmol) of tert.-octylphenol, 3.46 g (25 mmol) of potassium carbonate was heated for 21 hours to 115° C. The reaction mixture was cooled to room temperature, the solid was isolated by filtration, the residue washed with water and dried at 70° C. under reduced pressure. The product was subjected to column chromatography using toluene petroleum ether 1:2 and 1:1 and toluene. 1.2 g (19%) of pure product were isolated.

Rf (toluene)=0.36.

¹H-NMR (300 MHz, CDCl₃) δ: 8.15 (4H, s), 7.27 (8H, d, J 6.9), 6.86 (8H, d, J 8.0), 6.01-5.83 (2H, m), 5.33-5.10 (4H, m), 4.73 (4H, d, J 5.3), 1.73 (8H, s), 1.36 (24H, s), 0.78 (36H, s).

Example II: Preparation of

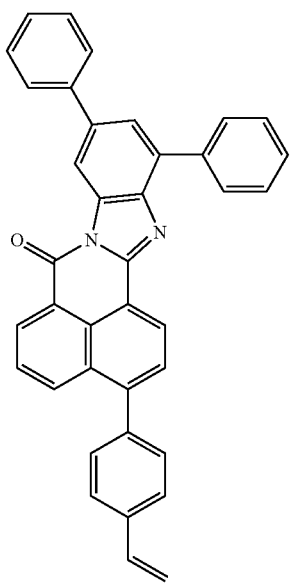

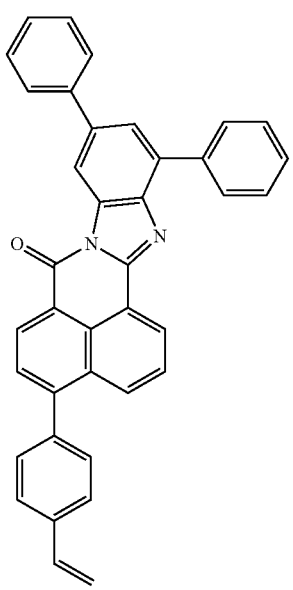

II.1 Preparation of

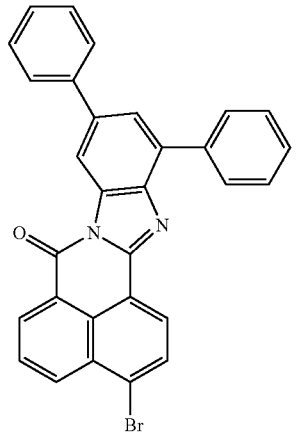

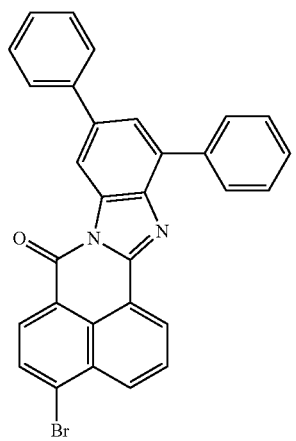

Under argon, 2.91 g (10 mmol) of 4-bromo-1,8-naphthalic anhydride and 3.18 g (12 mmol) of 1,2-diamino-3,5-diphenylbenzene (prepared according to the method described in example 19 of WO 2012/168395) were introduced with 1.84 g (10 mmol) of zinc acetate at room temperature into 30 mL of quinoline. The mixture was stirred under argon at 145° C. for 4 hours. The yellow solution was stirred at room temperature overnight. The red-brown suspension was stirred into 250 mL of 1 molar hydrochloric acid. The precipitated solid was filtered off with suction after 1 hour, the residue was twice more suspended in 100 mL each time of 1 molar hydrochloric acid and filtered off with suction, washed with 500 mL of hot demineralized water, then washed twice with 10 mL each time of methanol, and the orange residue was suction-dried with n-pentane. Yield: >99%, R_f (dichloromethane): 0.77.

II.2 Preparation of

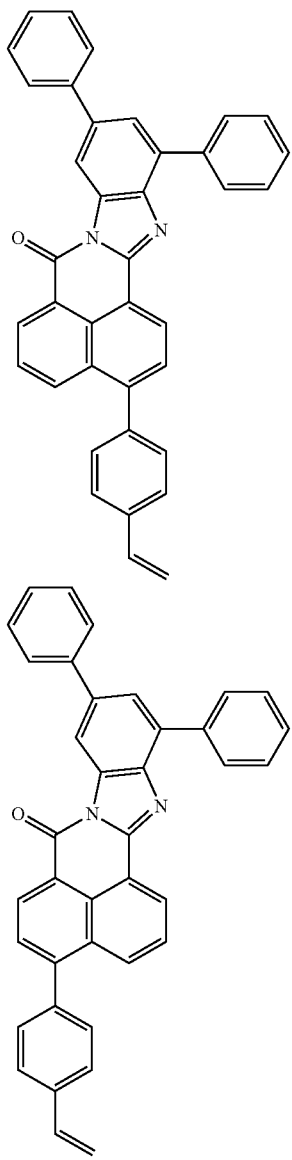

Example III: Preparation of

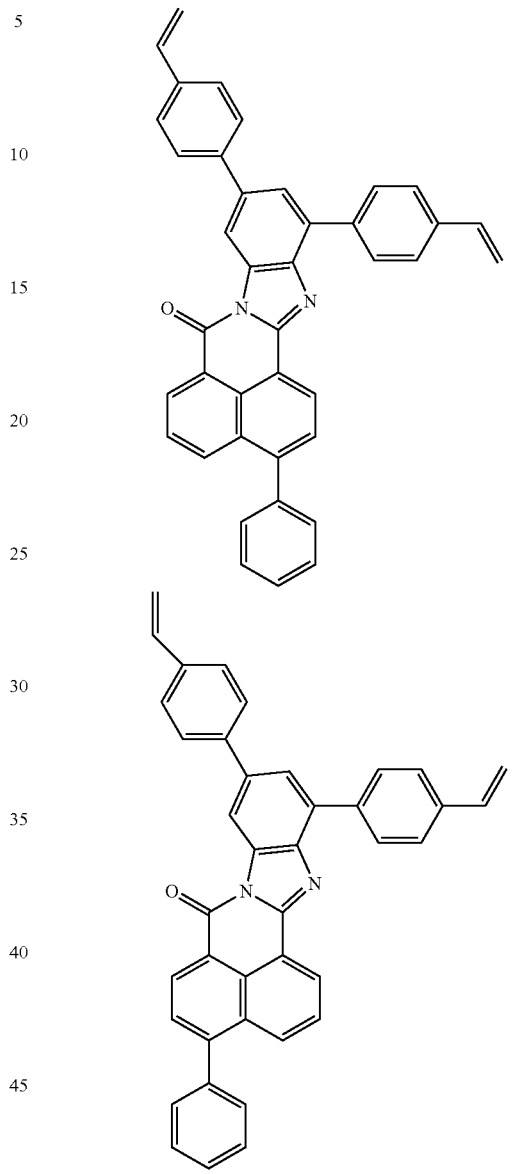

A mixture of 150 mL of toluene, 4.0 g (0.008 mol) of the isomeric mixture from example II.1, 1.18 g (0.008 mol) of 4-vinylphenylboronic acid, 1.1 g (0.008 mol) of potassium carbonate dissolved in 10 mL of water and 0.092 g (0.00008 mol) of tetrakis(triphenylphosphine)palladium was stirred at 85-90° C. for 4 hours. 0.1 g (0.68 mmol) of 4-vinylphenylboronic acid were added and the mixture stirred for further 4 hours. The reaction mixture was cooled to room temperature which results in the precipitation of product. The product was isolated by filtration, washed with methanol and water. The residue was dried, dissolved in 100 mL of hot toluene. 1 g of charcoal was added. The hot suspension was filtered, the residue washed with toluene and toluene was evaporated. Methanol was added and the product was isolated by filtration. 2.72 g (65%) of a yellow product was obtained. According to $^{13}$C-NMR the product consist of a 70:30 mixture of isomers.

III.1 2-nitro-4,6-bis(4-vinylphenyl)aniline 10 g (33.8 mmol) of 2,4-dibromo-6-nitroaniline were dissolved in 400 mL of toluene. 11 g (74.3 mmol) of (4-vinylphenyl)boronic acid, a solution of 18.3 g (132.4 mmol) of $K_2CO_3$ in water and 39 mg (0.034 mmol) of Pd[P($C_6H_5$)$_3$]$_4$ were added. The mixture was stirred at 85° C. for 4 hours. The reaction mixture was worked up with water. The organic layer was dried and the solvent was removed. The residue was purified by liquid chromatography with toluene. 10.6 g (93%) of a red oil was obtained.

TLC (toluene:petroleum ether 8:2): Rf=0.48.

III.2 3,5-bis(4-vinylphenyl)benzene-1,2-diamine 10.6 g (28.9 mmol) of the compound from example III.1, 250 mL of ethanol and 22.34 g (115.6 mmol) of Sn(II)Cl$_2$ were stirred at reflux for 19 hours. The solvent from the reaction mixture was removed. The residue was worked up with dichloromethane and sodium hydroxide solution. The organic layer was dried and the solvent was removed. 8.24 g (91%) of a yellow-orange solid was obtained.

TLC (toluene:petroleum ether 8:2): Rf=0

III.3 Preparation of

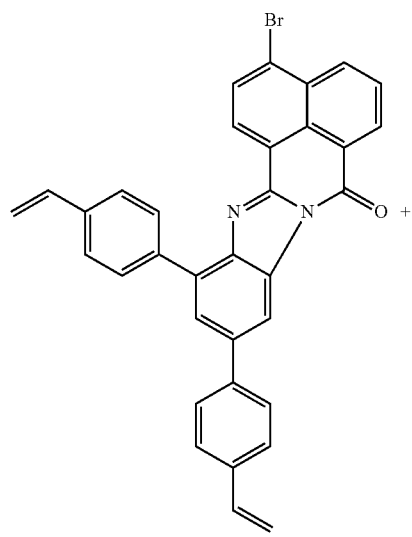

To a solution of 6.93 g (22.18 mmol) of the compound from example III.2 in 400 mL anisole were added 6.47 g (22.18 mmol) of 4-bromo-1,8-naphthalic anhydride, 21 mL (148 mmol) of triethylamine and 4.1 g (22.18 mmol) zinc acetate were added. The mixture was stirred at 100° C. for 22 hours. 1000 mL of methanol were added to the reaction mixture. The precipitated solid was filtered off, washed with methanol and dried under reduced pressure. 8.31 g (68%) of a red solid were obtained.

TLC (toluene:ethyl acetate 10:1): Rf=0.91

III.4 Preparation of

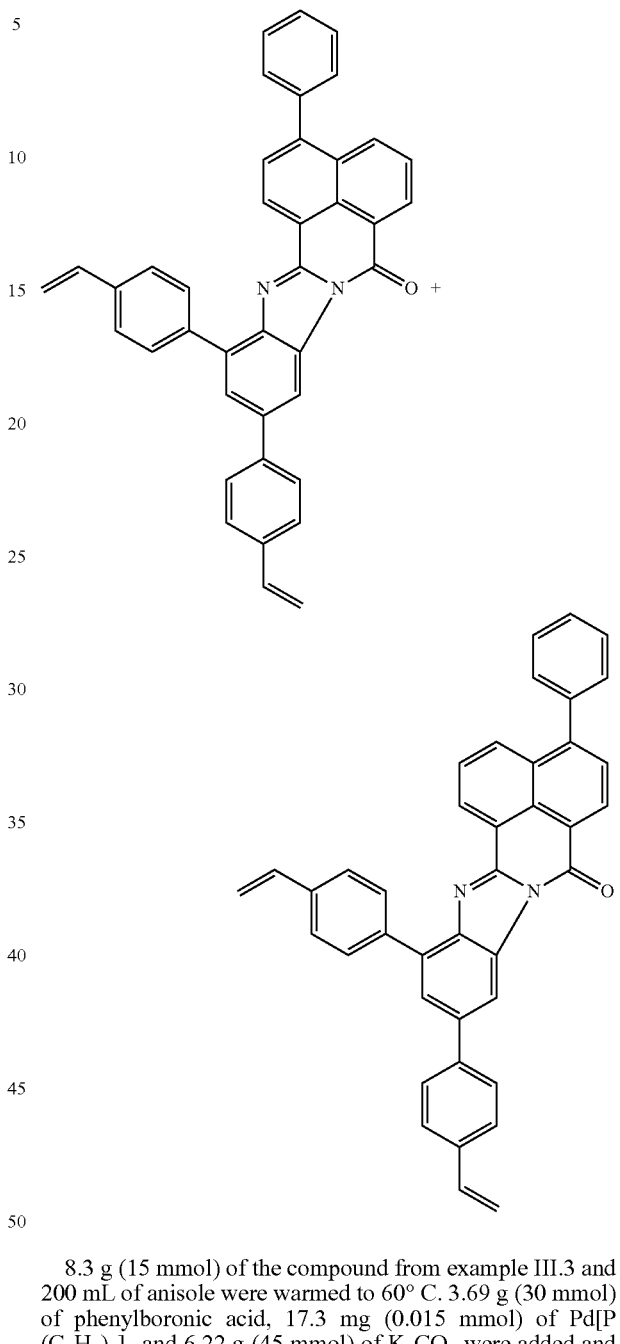

8.3 g (15 mmol) of the compound from example III.3 and 200 mL of anisole were warmed to 60° C. 3.69 g (30 mmol) of phenylboronic acid, 17.3 mg (0.015 mmol) of Pd[P(C$_6$H$_5$)$_3$]$_4$ and 6.22 g (45 mmol) of K$_2$CO$_3$ were added and the mixture was stirred at 90° C. for 6 hours. The reaction mixture was dropped in methanol and an orange solid was filtered off. After further purification by liquid chromatography with toluene, 3.1 g (37%) of an orange solid was obtained.

TLC (toluene:petroleum ether 4.1): Rf=0.4

Comparison with Other Compounds:

The compounds of examples I, II and III were compared to the following comparative compounds: N,N'-bis(2,6-diisopropylphenyl)-1,6,7,12-tetraphenoxy-3,4,9,10-perylenetetracarboxylic diimide, commercially available from BASF SE, Germany, and compound of example 10 of WO 2012/168395.

These comparative compounds are shown below

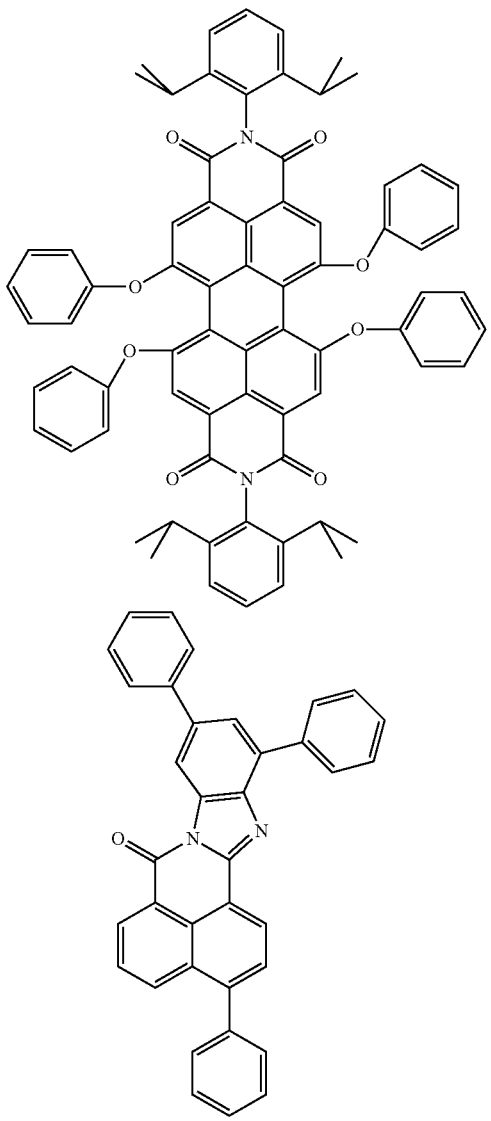

N,N'-bis(2,6-diisopropylphenyl)-1,6,7,12-tetraphenoxy-3,4,9,10-perylenetetracarboxylic diimide Compound of Example 10 of WO 2012/168395

II. Preparation of Copolymers of Organopolysiloxane Resins and Organic Fluorescent Dyes

II.1 General Procedure for the Preparation of the Copolymers

Materials Used:

Dow(1): Dow Corning® OE-6630 available from Dow Corning Co., USA; used without purification; two part, high refractive index, transparent, heat-cure, polymethylphenylsiloxane resin; part A and part B were to be mixed in a ratio 1:4.

Part A: contains the vinyl-containing polyphenylmethylsiloxane (average ratio of methyl/phenyl/vinyl is about 14/2/1, determined by $^1$H-NMR spectroscopy) and the platinum catalyst.

Part B: contains the silicon hydride containing polyphenylmethylsiloxane (average ratio of methyl/phenyl/hydride is about 3/1/1, determined by $^1$H-NMR spectroscopy).

IR spectrum of cured Dow(1): v: 3049, 3072 cm$^{-1}$ (C—H)$_{phenyl}$; 2953, 2909 (C—H); 1590, 1490, 1430 (C=V—C)$_{phenyl}$; 1413, 1257 (C—H [Si—CH$_3$]); 1115, 1024 (Si—O—Si); 784 (C—H [Si—(CH$_3$)$_2$]); 726, 694 cm$^{-1}$ (C—H [Si(CH$_3$)$_2$]).

Shin (1): Shin-Etsu Silicone KJR9022E, available from Shin-Etsu, Japan; used without purification; two part, low refractive index transparent, heat-cure, polydimethyl siloxane; part A and part B were to be mixed in a ratio 1:10. in the following Shin(1).

Part A: contains the vinyl-containing polydimethylsiloxane (average ratio methyl/vinyl is about 111/1, determined by $^1$H-NMR spectroscopy).

Part B: contains the hydride containing polysiloxane (average ratio of methyl/hydride is about 5/1, determined by $^1$H-NMR spectroscopy).

IR spectrum of cured Shin(1): v: 2960, 2902 (C—H); 1412, 1257 (C—H [Si—CH$_3$]); 1065, 1008 (Si—O—Si); 784 (C—H [Si—(CH$_3$)$_2$]).

Part A and part B of the polysiloxane of Dow(1) and Shin(1), respectively, were mixed as specified by the manufacturer. To this mixture was added a stock solution of dye (0.1% by weight, CHCl$_3$). A series of samples with a concentration of 100, 250, 500, 750, 1000, 1500, 2000, and 3000 ppm by weight of dye were prepared. The obtained mixture was degassed and the solvent was removed under reduced pressure (4 mbar, >30 min) before casting into PTFE (polytetrafluoroethylene) molds (30×10×1 mm). The mixtures were cured for 4 h at 150° C. The mean sample thickness is 1.11±0.09 mm.

Example 1: Reaction of the Compound of Example I with Dow(1)

Polymers were prepared according to the general procedure described above, wherein the dye is the compound from example I and the polysiloxane is Dow(1).

Example 2: Reaction of the Compound of Example I and Shin(1)

Polymers were prepared according to the general procedure described above, wherein the dye is the compound from example I and the polysiloxane is Shin(1).

Example 3: Reaction of Compound of Example I and Dow (1)

To the premixed components A and B of Dow(1) was added a stock solution with a concentration of 0.1% by weight of compound from example I in CHCl$_3$ to achieve a concentration of 0.03% by weight of compound of example I based on the amount of Dow(1). By stirring overnight, the solvent was removed from the mixture (12 h; 200 rpm; 25° C.). The degassed mixture was processed into a layer by means of a doctor blade (280 μm). The layers were cured for 4 h at 150° C.

Example 3a: Reaction of Compound of Example I and Dow (1)

To the premixed components A and B of Dow(1) was added a stock solution with a concentration of 0.1% by weight of compound from example I in CHCl₃ to achieve a concentration of 0.03% by weight of compound of example I based on the amount of Dow(1). In addition, 0.5% by weight of TiO₂, based on the amount of Dow(1) was added. By stirring overnight, the solvent was removed from the mixture (12 h; 200 rpm; 25° C.). The degassed mixture was processed into a layer by means of a doctor blade (280 μm). The layers were cured for 4 h at 150° C.

Example 4: Reaction of Compound of Example II and Dow (1)

The polymer was prepared in analogy to the procedure described in example 3, but using the compound of example II in an amount of 0.094% by weight, based on the amount of Dow(1) instead of the compound of example 1.

Example 4a: Reaction of Compound of Example II and Dow (1)

The polymer was prepared in analogy to the procedure described in example 3a, but using the compound of example II in an amount of 0.094% by weight, based on the amount of Dow(1) instead of the compound of example 1.

Example 5: Reaction of Compound of Example III and Dow (1)

The polymer was prepared in analogy to the procedure described in example 3, but using the compound of example III in an amount of 0.094% by weight, based on the amount of Dow(1) instead of the compound of example 1.

Example 5a: Reaction of Compound of Example III and Dow (1)

The polymer was prepared in analogy to the procedure described in example 3a, but using the compound of example III in an amount of 0.094% by weight, based on the amount of Dow(1) instead of the compound of example 1.

Comparative Examples

The polymers of examples 1 through 5 were compared to the following comparative samples:

Comparative Example 1: N,N'-bis(2,6-diisopropylphenyl)-1,6,7,12-tetraphenoxy-3,4,9,10-perylenetetracarboxylic diimide Dispersed in Dow(1)

The procedure of example 1 was repeated but N,N'-bis(2,6-diisopropylphenyl)-1,6,7,12-tetraphenoxy-3,4,9,10-perylenetetracarboxylic diimide was instead of the compound of example 1.

Comparative Example 2: N,N'-bis(2,6-diisopropylphenyl)-1,6,7,12-tetraphenoxy-3,4,9,10-perylenetetracarboxylic diimide Dispersed in Shin(1)

The procedure of example 2 was repeated but using N,N'-bis(2,6-diisopropylphenyl)-1,6,7,12-tetraphenoxy-3,4,9,10-perylenetetracarboxylic diimide instead of the compound of example 1.

Comparative Example 3: N,N'-bis(2,6-diisopropylphenyl)-1,6,7,12-tetraphenoxy-3,4,9,10-perylenetetracarboxylic diimide Dispersed in Dow(1)

The procedure of example 3 was repeated but N,N'-bis(2,6-diisopropylphenyl)-1,6,7,12-tetraphenoxy-3,4,9,10-perylenetetracarboxylic diimide was instead of the compound of example 1.

Comparative Example 3a: N,N'-bis(2,6-diisopropylphenyl)-1,6,7,12-tetraphenoxy-3,4,9,10-perylenetetracarboxylic diimide Dispersed in Dow(1)

The procedure of example 3a was repeated but N,N'-bis(2,6-diisopropylphenyl)-1,6,7,12-tetraphenoxy-3,4,9,10-perylenetetracarboxylic diimide was used instead of the compound of example 1.

Comparative Example 4: Compound of Example 10 of WO 2012/168395 Dispersed in Dow(1)

The procedure of example 4 was repeated by using the compound of example 10 of WO 2012/168395 instead of the compound of example II.

Comparative Example 4a: Compound of Example 10 of WO 2012/168395 Dispersed in Dow(1)

The procedure of example 4a was repeated by using the compound of example 10 of WO 2012/168395 instead of the compound of example II.

The curable silicon resin compositions obtained in Examples 1, 2, 3, 3a, 4, 4a, 5 and 5a and Comparative Example 1, 2, 3, 3a, 4 and 4a were evaluated as follows:

III Fluorescence Spectroscopy and Fluorescent Quantum Yield Measurements

The fluorescent compounds of examples I, II and III were used to produce thin films of color converters by the method described in the following. The polymers used were polystyrene (PS 168 N from BASF) and polycarbonate (PC, Macrolon®2808 from Bayer). About 2.5 g of polymer and 0.015% to 0.039% by weight of dye were dissolved in about 5 mL of methylene chloride, and 0.5% by weight of TiO₂ (Kronos 2220) were dispersed therein, based in each case on the amount of polymer used. The exact composition of each converter is described in table 1. The solutions/dispersion obtained were coated onto a glass surface using an applicator frame (from Ericsen, wet film thickness 400 μm). After the solvent had dried off, the film was detached from the glass and dried in a vacuum drying cabinet at 50° C. overnight. Two circular film pieces of 80 to 85 μm thickness having a diameter of 15 mm were punched out of each film, and used as analysis samples.

Fluorescence quantum yields (FQY) of the analysis samples were measured with the C9920-02 quantum yield measuring system (from Hamamatsu). This was done by illuminating each of the samples with light of 445 to 455 nm in an integration sphere (Ulbricht sphere). By comparison with the reference measurement in the Ulbricht sphere without sample, the unabsorbed fraction of the excitation light and the fluorescent light emitted by the sample are determined by means of a CCD spectrometer. Integration of the intensities over the spectrum of the unabsorbed excitation light or over that of the emitted fluorescent light gives the degree of absorption or fluorescence intensity or fluorescence quantum yield of each sample.

The absorption and emission of the dyes was characterized in dichloromethane (DCM) solution and in polymer matrix (PC and PS). The results are compiled in Table 1. In addition, the emission spectra of the polymers of examples 3, 4 and 5 and comparative examples 3 and 4 were recorded. The results are also compiled in Table 1.

TABLE 1

|  | Absorption maximum | Emission maximum | QY |
|---|---|---|---|
| compound of example I in DCM | 582 nm | 622 nm | 100% |
| 0.036% compound of example I in PS | — | 615 nm | 94% |
| 0.039% compound of example I in PC | — | 620 nm | 93% |
| compound of example II in DCM | 423 nm | 564 nm | 53% |
| 0.015% compound of example II in PC | — | 538 nm | 84% |
| compound of example III in DCM | — | 579 nm | 46% |
| 0.015% compound of example. III in PC | — | 548 nm | 82% |
| Polymer of example 3 | — | 615 nm | 92% |
| Comparative example 3 | — | 615 nm | 93% |
| Example 4 | — | 532 nm | 86% |
| Example 5 | — | 543 nm | 83% |
| Comparative example 4 | — | 532 nm | 87% |

It was found that the quantum yields of the inventive polymers compared to said of the comparative examples is nearly unchanged. In terms of normalized spectra, the polymer of example 3 shows an enhanced shoulder in comparison to the spectrum of comparative example 3. It was also found that emission spectra normalized to the maximum of example 4 is identical with that of comparative example 4.

IV. Photostability Measurement

The lifetimes of the polymer of examples 3a, 4a and 5a, respectively, as well as the lifetime of the comparative example 3a and comparative example 4a were evaluated. For this purpose, films were prepared. The composition is described in table 2. The solutions/dispersion obtained were coated onto a glass surface using an applicator frame (from Ericsen, wet film thickness 400 μm). After the solvent had dried off, the film was detached from the glass and dried in a vacuum drying cabinet at 50° C. overnight. Two circular film pieces of 80 to 85 μm thickness having a diameter of 15 mm were punched out of each film, and used as analysis samples.

Table 2 summarizes the T80 values, the time when the fluorescence (product QY*absorption) has reached 80% of its initial value.

TABLE 2

|  | T80 in air | T80 in N2 |
|---|---|---|
| Comparative example 3a | 22.8 days | 92.1 days |
| Example 3a | 41.7 days | >>100 days |
| Comparative example 4a | 23 h | 13 h |
| Example 4a | 82 h | 16 h |
| Example 5a | 142 h | 32 h |

As can be seen from table 2, the polymer according to the inventions exhibits an improved photochemical stability in comparison to a polymer with an organic fluorescent dye of prior art.

V. Swelling and Leaching

Leaching experiments were carried out with the polymers from examples 1 and 2, and comparative examples 1 and 2 in a toluene solution for a period of 24 h. In examples 1 and 2, the concentration of the compound from example I was 100 and 3000 ppm by weight, respectively, for each polymer and in the comparative examples 1 and 2, the concentration of N,N'-bis(2,6-diisopropylphenyl)-1,6,7,12-tetraphenoxy-3,4,9,10-perylenetetracarboxylic diimide was also 100 and 3000 ppm by weight, respectively, for each polymer.

It is observed from swelling studies in toluene that in the polymers from examples 1 and 2, the compound from example I completely stayed in the matrix over a period of 24 hour, whereas in comparative examples 1 and 2, N,N'-bis(2,6-diisopropylphenyl)-1,6,7,12-tetraphenoxy-3,4,9,10-perylenetetracarboxylic diimide was entirely leached out within 24 hours. The visual impression was supported by UV-VIS spectroscopy of the diluted toluene solution after the leaching experiments. Only the spectra of comparative examples 1 and 2 show the typical dye absorption bands of N,N'-bis(2,6-diisopropylphenyl)-1,6,7,12-tetraphenoxy-3,4,9,10-perylenetetracarboxylic diimide at 575 nm. It is concluded, therefore, that in examples 1 and 2 the compound of example I is covalently bonded to the polysiloxane, whereas in comparative examples 1 and 2, N,N'-bis(2,6-diisopropylphenyl)-1,6,7,12-tetraphenoxy-3,4,9,10-perylenetetracarboxylic diimide is not bonded to the polysiloxane but dispersed in the polysiloxane matrix.

The invention claimed is:

1. A curable silicone resin composition comprising a curable silicone resin mixture and at least one $C_2$-$C_3$-alkenyl-substituted compound (I) which is a compound having the formula (I-A. 1):

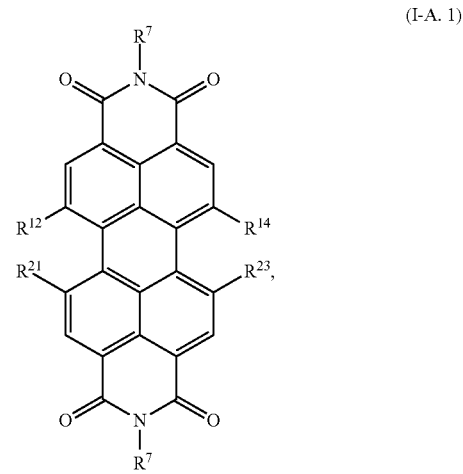

(I-A. 1)

each $R^7$ is independently vinyl or 2-propenyl; and
$R^{12}$, $R^{14}$, $R^{21}$ and $R^{23}$ are independently phenoxy which is substituted by a branched $C_3$-$C_{24}$-alkyl radical;
or the $C_2$-$C_3$-alkenyl-substituted compound (I) is a compound having the formula (I-B.1)

wherein
n is 2;
one of $R^5$ and $R^6$ is hydrogen and the other is unsubstituted phenyl, and
each $R^8$ is phenyl substituted with one or two $C_2$-$C_3$-alkenyl groups;
or
one of $R^5$ and $R^6$ is hydrogen and the other is phenyl substituted with one or two $C_2$-$C_3$-alkenyl groups, and
each $R^8$ is unsubstituted phenyl;
where the curable silicone resin mixture comprises a curable organopolysiloxane and a hydrosilylation catalyst, where the curable organopolysiloxane contains silicon bonded hydrogen atoms which can undergo a hydrosilylation reaction in the presence of the hydrosilylation catalyst.

2. A polymer comprising in copolymerized form:
at least one $C_2$-$C_3$-alkenyl-substituted compound of claim 1; and
an organopolysiloxane C which contains silicon bonded hydrogen atoms which can undergo a hydrosilylation reaction in the presence of the hydrosilylation catalyst.

3. The polymer of claim 2, wherein the organopolysiloxane C comprises in polymerized form:
an organopolysiloxane C.1 comprising at least two silicon-bonded $C_2$-$C_6$-alkenyl groups per molecule; and
an organopolysiloxane C.2 comprising at least two silicon-bonded hydrogen atoms per molecule.

4. The polymer of claim 3, wherein the organopolysiloxane C.1 further comprises at least one silicon-bonded $C_1$-$C_6$-alkyl group per molecule; and
wherein the organopolysiloxane C.2 further comprises at least one silicon-bonded $C_1$-$C_6$-alkyl group per molecule.

5. The polymer of claim 3, wherein the organopolysiloxane C.1, further comprises at least one silicon-bonded $C_1$-$C_6$-alkyl group and at least one silicon bonded $C_6$-$C_{10}$-aryl group, which is unsubstituted or substituted by methyl, per molecule; and
wherein the organopolysiloxane C.2, further comprises at least one silicon-bonded $C_1$-$C_6$-alkyl group and at least one silicon bonded $C_6$-$C_{10}$-aryl group, which is unsubstituted or substituted by methyl, per molecule.

6. The polymer of claim 2, wherein the at least one $C_2$-$C_3$-alkenyl-substituted compound is present in an amount of 0.0001 to 1% by weight, based on the amount of the organopolysiloxane C.

7. The polymer of claim 2, further comprising at least one component selected from the group consisting of an inorganic phosphor, an organic fluorescent compound different from the compound of formula I, a scattering body, a filler, a heat stabilizer, an antioxidant, a lubricant, a light stabilizer, a dispersant, an antistatic agent, an antifoamer, a solvent, an anti-aging agent, a radical inhibitor, a polymerization inhibitor, a flame retardant, and an adhesion-imparting agent.

8. A lighting device, comprising at least one blue LED with a center wavelength of emission between 400 nm and 480 nm and the polymer of claim 2,
wherein the polymer is disposed in front of the LED in its emission direction, and
wherein the polymer is not spaced from the LED.

9. An LED device, comprising the polymer of claim 2 and an LED.

10. The LED device of claim 9,
wherein the LED is a blue LED emitting light with a center wavelength of emission between 400 nm and 480 nm that is converted by the polymer into light of a second, longer wavelength, or
wherein the LED is a white LED emitting light having a correlated color temperature between 3,000 K and 20,000 K which is converted by the polymer into a white light having a lower correlated color temperature.

11. A compound of formula (I-A.1),

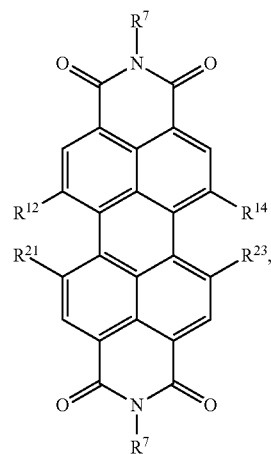

wherein:
each $R^7$ is independently a vinyl or a 2-propenyl; and
$R^{12}$, $R^{14}$, $R^{21}$, $R^{23}$, $R^{31}$, and $R^{33}$ are independently a phenoxy, which is substituted by a branched $C_3$-$C_{24}$-alkyl radical.

12. A compound of (I-B.1)

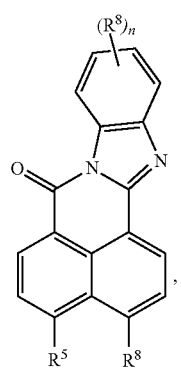

wherein n is 2;

one of $R^5$ and $R^6$ is bydrogen and the other is unsubstituted phenyl, and each $R^8$ is phenyl substituted with one or two $C_2$-$C_3$-alkenyl groups;

or one of $R^5$ and $R^6$ is hydrogen and the other is phenyl substituted with one or two $C_2$-$C_3$-alkenyl groups, and each $R_8$ is unsubstituted phenyl.

13. The LED device of claim 9, wherein the polymer emits a light in a visible spectral range.

14. The LED device of claim 9, wherein the polymer emits a light which is a data transmission.

* * * * *